US012749081B2

(12) United States Patent
Seshadri

(10) Patent No.: US 12,749,081 B2
(45) Date of Patent: Sep. 29, 2026

(54) SYSTEM AND METHOD FOR DYNAMIC NETWORK INFRASTRUCTURE, PROOF OF ACHIEVEMENT, AND CONTEXTUAL NFT GENERATION

(71) Applicant: Healthy Engage LLC, Frisco, TX (US)

(72) Inventor: Ravi Seshadri, Frisco, TX (US)

(73) Assignee: Healthy Engage LLC, Frisco, TX (US)

( * ) Notice: Subject to any disclaimer, the term of this patent is extended or adjusted under 35 U.S.C. 154(b) by 26 days.

(21) Appl. No.: 19/055,074

(22) Filed: Feb. 17, 2025

(65) Prior Publication Data

US 2025/0272431 A1 Aug. 28, 2025

Related U.S. Application Data

(60) Provisional application No. 63/558,760, filed on Feb. 28, 2024.

(51) Int. Cl.

| | |
|---|---|
| ***G06F 21/62*** | (2013.01) |
| ***G06F 21/16*** | (2013.01) |
| ***G06F 21/60*** | (2013.01) |
| ***G16H 10/60*** | (2018.01) |

(52) U.S. Cl.

CPC .......... *G06F 21/6245* (2013.01); *G06F 21/16* (2013.01); *G06F 21/602* (2013.01); *G16H 10/60* (2018.01)

(58) Field of Classification Search

CPC .... G06F 21/6245; G06F 21/16; G06F 21/602; G16H 10/60

See application file for complete search history.

(56) References Cited

U.S. PATENT DOCUMENTS

| | | | | |
|---|---|---|---|---|
| 9,043,602 | B1 * | 5/2015 | Krieger | H04W 12/06 713/181 |
| 9,590,958 | B1 * | 3/2017 | Howell | H04L 63/061 |
| 10,769,682 | B1 * | 9/2020 | McDonald | G06F 3/0488 |
| 10,893,385 | B1 * | 1/2021 | Berardino | H04W 4/029 |
| 11,100,502 | B1 * | 8/2021 | Rainey | H04L 9/3263 |
| 11,244,032 | B1 * | 2/2022 | Nguyen | G06F 9/547 |
| 11,494,171 | B1 * | 11/2022 | Acharya | H04L 9/0861 |

(Continued)

FOREIGN PATENT DOCUMENTS

| | | | |
|---|---|---|---|
| EP | 4310763 | A1 | 1/2024 |
| WO | 2022133330 | A1 | 6/2022 |

*Primary Examiner* — Aravind K Moorthy

(57) ABSTRACT

A method includes retrieving a plurality of data from one or more data sources, generating, a contextual NFT based on at least a portion of the plurality of data, executing one or more ephemeral computing operations. The method also includes, as a result of deletion of an ephemeral record created during the ephemeral computing operations, generating a unique reference pointing to an original timestamped source of at least a portion of the plurality of data associated with an original recipient, and performing source tracking to track the unique reference associated with the original recipient. The method also includes determining a proof of achievement score based on results of the one or more hybrid transactions, performing analysis and adjudication using a transaction repository and the at least one smart contract, and determining and output a proof of acknowledgement result based on the analysis and adjudication.

20 Claims, 9 Drawing Sheets

(56) References Cited

U.S. PATENT DOCUMENTS

| | | | | |
|---|---|---|---|---|
| 11,677,846 | B1 * | 6/2023 | Howes | H04L 67/535<br>709/224 |
| 11,688,158 | B1 * | 6/2023 | Jain | H04L 9/3247<br>382/190 |
| 11,748,818 | B1 * | 9/2023 | Wince | G06Q 40/08<br>705/2 |
| 11,880,888 | B1 * | 1/2024 | Gold | G06Q 10/00 |
| 12,013,845 | B1 * | 6/2024 | Kavali | G06F 16/21 |
| 12,028,208 | B1 * | 7/2024 | Hsiao | G06F 16/26 |
| 12,175,454 | B1 * | 12/2024 | Kurani | G06Q 20/3674 |
| 12,298,980 | B1 * | 5/2025 | Raman | G06F 16/24573 |
| 12,299,751 | B1 | 5/2025 | Downs et al. | |
| 12,321,924 | B1 * | 6/2025 | Kurani | G06Q 40/04 |
| 12,554,885 | B1 * | 2/2026 | Beebe | G06F 21/6254 |
| 12,619,787 | B2 * | 5/2026 | Silva | G06F 21/64 |
| 2002/0136410 | A1 * | 9/2002 | Hanna | H04L 9/088<br>380/277 |
| 2015/0074757 | A1 * | 3/2015 | Sharma | G06F 21/45<br>726/2 |
| 2016/0226944 | A1 * | 8/2016 | Hsiao | H04L 43/028 |
| 2017/0103425 | A1 * | 4/2017 | Christofi | G06Q 30/0269 |
| 2017/0235792 | A1 * | 8/2017 | Mawji | G06F 16/29<br>707/769 |
| 2018/0013714 | A1 * | 1/2018 | Leach | G06F 16/22 |
| 2018/0060496 | A1 * | 3/2018 | Bulleit | H04L 9/0643 |
| 2018/0367540 | A1 * | 12/2018 | Miranda | H04L 63/0478 |
| 2018/0373750 | A1 * | 12/2018 | Zhu | G06F 9/526 |
| 2019/0026322 | A1 * | 1/2019 | Gerweck | G06Q 30/02 |
| 2019/0097964 | A1 * | 3/2019 | Martinazzi | H04L 51/52 |
| 2019/0303385 | A1 * | 10/2019 | Ching | H04L 63/1433 |
| 2019/0361917 | A1 * | 11/2019 | Tran | H04W 12/108 |
| 2020/0090188 | A1 * | 3/2020 | Wince | H04L 9/3247 |
| 2020/0226285 | A1 * | 7/2020 | Bulleit | G06F 21/33 |
| 2020/0273122 | A1 * | 8/2020 | Sahagen | G06Q 50/163 |
| 2020/0367129 | A1 * | 11/2020 | Raheem | G06F 16/1824 |
| 2020/0410559 | A1 * | 12/2020 | Qaudeer | H04M 15/50 |
| 2021/0056637 | A1 * | 2/2021 | Downs | G06Q 40/08 |
| 2021/0182793 | A1 * | 6/2021 | Patel | G06Q 20/40155 |
| 2021/0192516 | A1 * | 6/2021 | Derosa-Grund | H04L 9/3247 |
| 2021/0281480 | A1 * | 9/2021 | Gonzalez Prieto | H04L 41/145 |
| 2021/0389932 | A1 * | 12/2021 | Mandia | G06F 8/20 |
| 2022/0012731 | A1 * | 1/2022 | Derosa-Grund | G06F 16/2365 |
| 2022/0139566 | A1 * | 5/2022 | Gardina | G16H 50/20<br>705/2 |
| 2022/0188819 | A1 * | 6/2022 | Ognjanovic | H04L 9/3263 |
| 2022/0222245 | A1 * | 7/2022 | Pezeshki | G06F 16/2379 |
| 2022/0309489 | A1 * | 9/2022 | Kahn | G06Q 20/367 |
| 2022/0327112 | A1 * | 10/2022 | Roth | G06F 16/2379 |
| 2022/0379203 | A1 * | 12/2022 | Owens | G06N 20/00 |
| 2022/0415460 | A1 * | 12/2022 | Dershem | G16H 10/60 |
| 2023/0004423 | A1 * | 1/2023 | Fatahi | G06Q 20/065 |
| 2023/0011621 | A1 * | 1/2023 | Jakobsson | H04L 9/3213 |
| 2023/0044043 | A1 * | 2/2023 | Johnson | G06T 7/001 |
| 2023/0070586 | A1 * | 3/2023 | Kapur | G06Q 20/123 |
| 2023/0129576 | A1 * | 4/2023 | Root | G06Q 20/389<br>705/39 |
| 2023/0141593 | A1 * | 5/2023 | Ramer | G06Q 10/063112<br>705/7.42 |
| 2023/0186264 | A1 * | 6/2023 | Reyes | G06V 20/42<br>705/51 |
| 2023/0186291 | A1 * | 6/2023 | Haddad | G06Q 20/363<br>705/64 |
| 2023/0188600 | A1 * | 6/2023 | Sulibhavi | H04L 9/50<br>709/224 |
| 2023/0215282 | A1 * | 7/2023 | Sastry | G09B 5/00<br>434/367 |
| 2023/0239313 | A1 * | 7/2023 | Peters | H04L 63/1425<br>726/22 |
| 2023/0259640 | A1 * | 8/2023 | Metzler | G06F 21/6218<br>713/191 |
| 2023/0281606 | A1 * | 9/2023 | Jakobsson | H04L 9/50<br>705/67 |
| 2023/0298002 | A1 * | 9/2023 | Moiyallah, Jr. | G06Q 20/36<br>705/71 |
| 2023/0298016 | A1 * | 9/2023 | Osborn | H04L 63/12<br>705/41 |
| 2023/0315819 | A1 * | 10/2023 | Guy | G06F 21/12<br>726/28 |
| 2023/0325792 | A1 * | 10/2023 | Timpson | G06Q 10/30<br>705/69 |
| 2023/0325814 | A1 * | 10/2023 | Vijayan | G06Q 20/3829<br>705/66 |
| 2023/0351341 | A1 * | 11/2023 | Lyren | G06Q 30/06 |
| 2023/0351395 | A1 * | 11/2023 | Anastasia | G06Q 30/0185 |
| 2023/0360300 | A1 * | 11/2023 | De Brouwer | G06Q 50/184 |
| 2023/0367566 | A1 * | 11/2023 | Dubrofsky | G06F 8/427 |
| 2023/0385815 | A1 * | 11/2023 | Jakobsson | G06Q 20/36 |
| 2023/0396453 | A1 * | 12/2023 | Jain | H04L 9/3213 |
| 2024/0045774 | A1 * | 2/2024 | Wang | G06F 11/1451 |
| 2024/0070234 | A1 * | 2/2024 | Wells | G06F 21/1014 |
| 2024/0070662 | A1 * | 2/2024 | Binder | G06Q 20/223 |
| 2024/0086384 | A1 * | 3/2024 | Soon-Shiong | G06F 16/2255 |
| 2024/0089247 | A1 * | 3/2024 | Singh | H04L 9/50 |
| 2024/0095220 | A1 * | 3/2024 | Isaacs | G06F 16/955 |
| 2024/0095720 | A1 * | 3/2024 | Binder | H04L 67/02 |
| 2024/0104173 | A1 * | 3/2024 | Tiseanu | G06F 21/31 |
| 2024/0144242 | A1 * | 5/2024 | Collins | H04L 9/50 |
| 2024/0161118 | A1 * | 5/2024 | Sarkisyan | G06Q 20/3674 |
| 2024/0171393 | A1 * | 5/2024 | Bathen | H04L 9/30 |
| 2024/0185191 | A1 * | 6/2024 | Bernardi | G06Q 20/065 |
| 2024/0193656 | A1 * | 6/2024 | Collen | G06Q 30/0185 |
| 2024/0201969 | A1 * | 6/2024 | Silverstein | H04L 9/3239 |
| 2024/0214194 | A1 | 6/2024 | Kapur et al. | |
| 2024/0249289 | A1 * | 7/2024 | Chiapuzio | G06Q 20/065 |
| 2024/0265223 | A1 * | 8/2024 | Binder | H04L 9/50 |
| 2024/0265473 | A1 * | 8/2024 | Farzanfar | G06Q 10/40 |
| 2024/0273654 | A1 * | 8/2024 | Kannaiyan | G06Q 20/1235 |
| 2024/0281504 | A1 * | 8/2024 | Collomosse | H04L 9/3213 |
| 2024/0303647 | A1 * | 9/2024 | Henderson | G06Q 20/389 |
| 2024/0311910 | A1 * | 9/2024 | van Schouwen | G06Q 20/389 |
| 2024/0345890 | A1 * | 10/2024 | Randhi | G06F 9/505 |
| 2024/0364504 | A1 * | 10/2024 | Alston | H04L 9/0894 |
| 2024/0370865 | A1 * | 11/2024 | Bernardi | G06Q 20/36 |
| 2025/0077578 | A1 * | 3/2025 | Bowman | G06F 16/9024 |
| 2025/0077625 | A1 * | 3/2025 | Coleman | G06F 21/1014 |
| 2025/0104059 | A1 * | 3/2025 | Mashkevich | G06Q 20/389 |
| 2025/0217752 | A1 * | 7/2025 | Dahiya | G06F 8/71 |
| 2025/0217785 | A1 * | 7/2025 | Singh | G06Q 10/40 |
| 2025/0272600 | A1 * | 8/2025 | Singh | G06N 20/00 |

* cited by examiner

SYSTEM AND METHOD FOR DYNAMIC NETWORK INFRASTRUCTURE, PROOF OF ACHIEVEMENT, AND CONTEXTUAL NFT GENERATION

CROSS-REFERENCE TO RELATED APPLICATION AND PRIORITY CLAIM

This application claims priority under 35 U.S.C. § 119 (e) to U.S. Provisional Patent Application No. 63/558,760 filed on Feb. 28, 2024, which is hereby incorporated by reference in its entirety.

TECHNICAL FIELD

This disclosure relates generally to blockchain and machine learning systems. More specifically, this disclosure relates to a system and method for dynamic network infrastructure, proof of achievement, and contextual NFT generation.

BACKGROUND

The healthcare industry is rapidly evolving and so are the options available to support it. However, current technological systems for monitoring patients and aspects of their healthcare are antiquated and rely on incomplete data and poor decision-making solutions.

SUMMARY

This disclosure relates to a system and method for dynamic network infrastructure, proof of achievement, and contextual NFT generation.

In one aspect, a system includes at least one processing device configured to retrieve a plurality of data from one or more data sources. The at least one processing device is also configured to generate, using a blockchain, a contextual non-fungible token (NFT) based on at least a portion of the plurality of data. The at least one processing device is also configured to execute one or more ephemeral computing operations in which the at least one processing device is further configured to determine whether access to the contextual NFT is allowed under at least one smart contract, grant, based on the determination, the access to the contextual NFT and associated records pursuant to the at least one smart contract, and analyze, using a reasoning engine configured to execute one or more machine learning models, and based on the at least one smart contract, a transaction event needing consensus among multiple parties. The at least one processing device is also configured to, as a result of deletion of an ephemeral record created during the ephemeral computing operations, generate a unique reference pointing to an original timestamped source of at least a portion of the plurality of data associated with an original recipient. The at least one processing device is also configured to perform source tracking to track the unique reference associated with the original recipient. The at least one processing device is also configured to receive results of one or more hybrid transactions stored in a transaction repository using the plurality of data. The at least one processing device is also configured to determine, using the reasoning engine, a proof of achievement score based on the results of the one or more hybrid transactions. The at least one processing device is also configured to perform analysis and adjudication using the transaction repository and the at least one smart contract. The at least one processing device is also configured to determine and output a proof of acknowledgement result based on the analysis and adjudication.

In another aspect, a method includes retrieving a plurality of data from one or more data sources. The method also includes generating, using a blockchain, a contextual non-fungible token (NFT) based on at least a portion of the plurality of data. The method also includes executing one or more ephemeral computing operations, including determining whether access to the contextual NFT is allowed under at least one smart contract, granting, based on the determination, the access to the contextual NFT and associated records pursuant to the at least one smart contract, and analyzing, using a reasoning engine configured to execute one or more machine learning models, and based on the at least one smart contract, a transaction event needing consensus among multiple parties. The method also includes, as a result of deletion of an ephemeral record created during the ephemeral computing operations, generating a unique reference pointing to an original timestamped source of at least a portion of the plurality of data associated with an original recipient. The method also includes performing source tracking to track the unique reference associated with the original recipient. The method also includes receiving results of one or more hybrid transactions stored in a transaction repository using the plurality of data. The method also includes determining, using the reasoning engine, a proof of achievement score based on the results of the one or more hybrid transactions. The method also includes performing analysis and adjudication using the transaction repository and the at least one smart contract. The method also includes determining and outputting a proof of acknowledgement result based on the analysis and adjudication.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B. Further, as used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smartphone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic accessory, an electronic tattoo, a smart mirror, or a smart watch).

Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such as APPLETV or GOOGLE TV), a smart speaker or speaker with an integrated digital assistant (such as APPLE HOMEPOD or AMAZON ECHO), a gaming console (such as an XBOX, PLAYSTATION, or NINTENDO consoles), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IoT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to various embodiments of this disclosure, an electronic device may be one or a combination of the above-listed devices. The electronic device disclosed here is not limited to the above-listed devices and may include any other electronic devices now known or later developed.

In the following description, electronic devices are described with reference to the accompanying drawings, according to various embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112 (f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112 (f).

BRIEF DESCRIPTION OF THE DRAWINGS

For a more complete understanding of this disclosure and its advantages, reference is now made to the following description taken in conjunction with the accompanying drawings, in which like reference numerals represent like parts.

DETAILED DESCRIPTION

Figure 1:
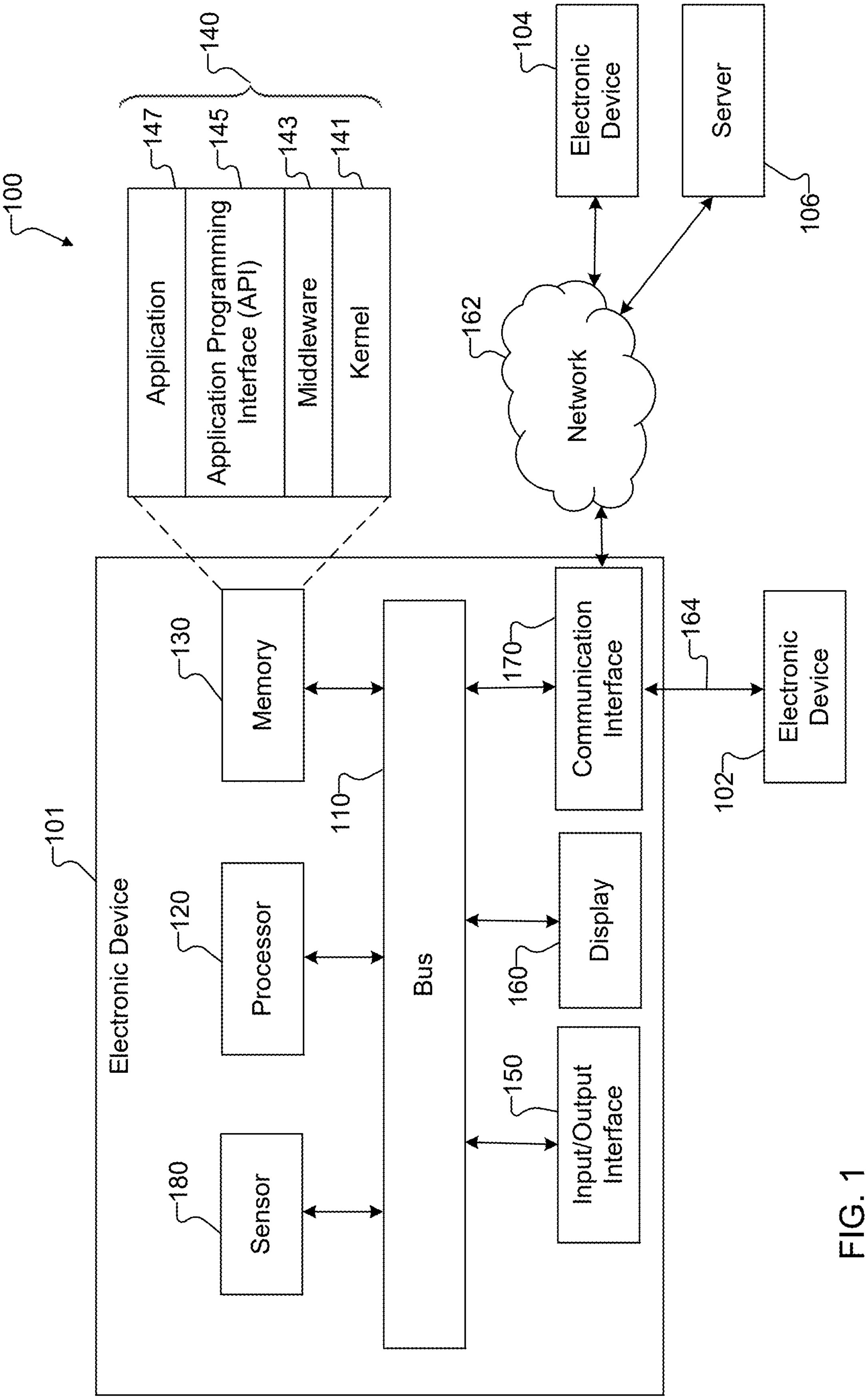
FIG. 1 illustrates an example network configuration including an electronic device in accordance with this disclosure.

FIGS. 1 through 9, discussed below, and the various embodiments of this disclosure are described with reference to the accompanying drawings. However, it should be appreciated that this disclosure is not limited to these embodiments, and all changes and/or equivalents or replacements thereto also belong to the scope of this disclosure. The same or similar reference denotations may be used to refer to the same or similar elements throughout the specification and the drawings.

As noted above, the healthcare industry is rapidly evolving and so are the options available to support it. However, current technological systems for monitoring patients and aspects of their healthcare are antiquated and rely on incomplete data and poor decision-making solutions.

In various embodiments, this disclosure provides an artificial intelligence (AI)-powered and blockchain-enabled system that acts as a patient-centric data record custodian for generating contextual non-fungible tokens (NFTs) for secure and efficient patient financial record creation, management, access, and sharing of patient financial records. The system facilitates selective sharing of financial record data with authorized parties while ensuring privacy, security, and control for the patient. In various embodiments, components and functionalities of the AI-powered system for generating contextual NFTs for patient financial records include an NFT generation platform that utilizes advanced AI techniques, such as natural language processing and machine learning algorithms, to analyze patient financial records and generate contextual NFTs that represent the value and uniqueness of each record. The platform ensures the secure creation, management, and transfer of NFTs among parties.

In various embodiments, components and functionalities of the AI-powered system for generating contextual NFTs for patient financial records also include an electronic financial record data block that is a secure, encrypted, storage component that houses patient financial records, ensuring data integrity and privacy. AI-driven data preprocessing and standardization techniques are employed to ensure data consistency and compatibility across different formats and sources.

In various embodiments, components and functionalities of the AI-powered system for generating contextual NFTs for patient financial records also include an account management server that incorporates a blockchain to provide a decentralized, tamper-proof ledger that manages patient financial records, NFT transactions, and access rights. The blockchain ensures transparency, trust, and immutability in the record-keeping process, facilitating collaboration among parties.

In various embodiments, components and functionalities of the AI-powered system for generating contextual NFTs for patient financial records also include an NFT brokerage that provides an intermediary service that facilitates the exchange of NFTs between parties, such as patients, healthcare providers, insurers, and other authorized parties. The NFT brokerage enables secure and efficient trading of NFTs representing access rights to patient financial records.

In various embodiments, components and functionalities of the AI-powered system for generating contextual NFTs for patient financial records also include smart contracts that are digitally enforced agreements that govern the terms and conditions for sharing patient financial records and exchanging NFTs. Smart contracts automate the execution of transactions and ensure compliance with privacy regulations and patient preferences.

In various embodiments, components and functionalities of the AI-powered system for generating contextual NFTs for patient financial records also include an AI-driven event detection and notification system using advanced AI algorithms that are used to monitor NFT transactions and identify significant events or anomalies associated with the NFT construct. Patients and other parties can receive real-time notifications of these events, ensuring timely intervention and enhanced control.

In various embodiments, the present disclosure provides an AI-powered distributed consensus system for hybrid (human and machine) transactions, focusing on rapidity, irreversibility, and agreement. This system aims to enhance the traditional POA approach by incorporating advanced AI techniques and enabling autonomous recommendation of agreement to foster a robust ecosystem of participants. The unique POA system of this disclosure involves all interested parties exchanging relevant activities, while a sophisticated reasoning engine facilitates the generation of a POA score, signifying relative achievement with respect to the original agreement or contract.

In various embodiments, the present disclosure provides an AI-powered distributed consensus algorithm for hybrid (human and machine) transactions, focusing on rapidity, irreversibility, and agreement. This system improves upon traditional poof of achievement (POA) approaches by incorporating advanced AI techniques and enabling autonomous recommendation of agreement to foster a robust ecosystem of participants. The proposed POA algorithm involves all interested parties exchanging relevant activities, while a sophisticated reasoning engine facilitates the generation of a POA score, signifying relative achievement with respect to the original agreement or contract.

In various embodiments, the present disclosure also provides an innovative, AI-powered distributed consensus system for secure, monitored, and automated exchange of sensitive information between trusted parties, all with consumer consent. This system allows for distributed consensus, monitoring, and automatic exchange of sensitive information between trusted parties for the purposes of an activity. This system employs a dynamic network infrastructure, ephemeral record management, and advanced AI techniques to enable transparent and efficient information sharing while ensuring data privacy and security. The system features an ephemeral record infrastructure that deletes sensitive data from local storage of recipients after a specific duration and/or confirmation event, replacing the deleted record with a unique reference pointer to the original time-stamped source for legal and reference purposes. The source tracks all unique references to the original recipient, and the authority of the network can add an "Observer/Auditor" to the unique reference in consensus with two or more authorities in a multi-authority POA network.

FIG. 1 illustrates an example network configuration 100 including an electronic device in accordance with this disclosure. The embodiment of the network configuration 100 shown in FIG. 1 is for illustration only. Other embodiments of the network configuration 100 could be used without departing from the scope of this disclosure.

According to embodiments of this disclosure, an electronic device 101 is included in the network configuration 100. The electronic device 101 can include at least one of a bus 110, a processor 120, a memory 130, an input/output (I/O) interface 150, a display 160, a communication interface 170, or a sensor 180. In some embodiments, the electronic device 101 may exclude at least one of these components or may add at least one other component. The bus 110 includes a circuit for connecting the components 120-180 with one another and for transferring communications (such as control messages and/or data) between the components.

The processor 120 includes one or more processing devices, such as one or more microprocessors, microcontrollers, digital signal processors (DSPs), application specific integrated circuits (ASICs), or field programmable gate arrays (FPGAs). In some embodiments, the processor 120 includes one or more of a central processing unit (CPU), an application processor (AP), a communication processor (CP), or a graphics processor unit (GPU). The processor 120 is able to perform control on at least one of the other components of the electronic device 101 and/or perform an operation or data processing relating to communication or other functions.

The memory 130 can include a volatile and/or non-volatile memory. For example, the memory 130 can store commands or data related to at least one other component of the electronic device 101. According to embodiments of this disclosure, the memory 130 can store software and/or a program 140. The program 140 includes, for example, a kernel 141, middleware 143, an application programming interface (API) 145, and/or an application program (or "application") 147. At least a portion of the kernel 141, middleware 143, or API 145 may be denoted an operating system (OS).

The kernel 141 can control or manage system resources (such as the bus 110, processor 120, or memory 130) used to perform operations or functions implemented in other programs (such as the middleware 143, API 145, or application 147). The kernel 141 provides an interface that allows the middleware 143, the API 145, or the application 147 to access the individual components of the electronic device 101 to control or manage the system resources. These functions can be performed by a single application or by multiple applications that each carries out one or more of these functions. The middleware 143 can function as a relay to allow the API 145 or the application 147 to communicate data with the kernel 141, for instance. A plurality of applications 147 can be provided. The middleware 143 is able to control work requests received from the applications 147, such as by allocating the priority of using the system resources of the electronic device 101 (like the bus 110, the processor 120, or the memory 130) to at least one of the plurality of applications 147. The API 145 is an interface allowing the application 147 to control functions provided from the kernel 141 or the middleware 143.

The I/O interface 150 serves as an interface that can, for example, transfer commands or data input from a user or other external devices to other component(s) of the electronic device 101. The I/O interface 150 can also output commands or data received from other component(s) of the electronic device 101 to the user or the other external device.

The display 160 includes, for example, a liquid crystal display (LCD), a light emitting diode (LED) display, an organic light emitting diode (OLED) display, a quantum-dot light emitting diode (QLED) display, a microelectromechanical systems (MEMS) display, or an electronic paper display. The display 160 can also be a depth-aware display, such as a multi-focal display. The display 160 is able to display, for example, various contents (such as text, images, videos, icons, or symbols) to the user. The display 160 can include a touchscreen and may receive, for example, a touch, gesture, proximity, or hovering input using an electronic pen or a body portion of the user.

The communication interface 170, for example, is able to set up communication between the electronic device 101 and an external electronic device (such as a first electronic device 102, a second electronic device 104, or a server 106). For example, the communication interface 170 can be connected with a network 162 or 164 through wireless or wired communication to communicate with the external electronic device. The communication interface 170 can be a wired or wireless transceiver or any other component for transmitting and receiving signals, such as images.

The electronic device 101 further includes one or more sensors 180 that can meter a physical quantity or detect an activation state of the electronic device 101 and convert metered or detected information into an electrical signal. The sensor(s) 180 can also include one or more buttons for touch input, one or more microphones, a gesture sensor, a gyroscope or gyro sensor, an air pressure sensor, a magnetic sensor or magnetometer, an acceleration sensor or accelerometer, a grip sensor, a proximity sensor, a color sensor (such as an RGB sensor), a bio-physical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can further include an inertial measurement unit, which can include one or more accelerometers, gyroscopes, and other components. In addition, the sensor(s) 180 can include a control circuit for controlling at least one of the sensors included here. Any of these sensor(s) 180 can be located within the electronic device 101.

The first external electronic device 102 or the second external electronic device 104 can be a wearable device or an electronic device-mountable wearable device (such as an HMD). When the electronic device 101 is mounted in the electronic device 102 (such as the HMD), the electronic device 101 can communicate with the electronic device 102 through the communication interface 170. The electronic device 101 can be directly connected with the electronic device 102 to communicate with the electronic device 102 without involving with a separate network. The electronic device 101 can also be an augmented reality wearable device, such as eyeglasses, that include one or more cameras.

The wireless communication is able to use at least one of, for example, long term evolution (LTE), long term evolution-advanced (LTE-A), 5th generation wireless system (5G), millimeter-wave or 60 GHz wireless communication, Wireless USB, code division multiple access (CDMA), wideband code division multiple access (WCDMA), universal mobile telecommunication system (UMTS), wireless broadband (WiBro), or global system for mobile communication (GSM), as a cellular communication protocol. The wired connection can include, for example, at least one of a universal serial bus (USB), high definition multimedia interface (HDMI), recommended standard 232 (RS-232), or plain old telephone service (POTS). The network 162 includes at least one communication network, such as a computer network (like a local area network (LAN) or wide area network (WAN)), Internet, or a telephone network.

The first and second external electronic devices 102 and 104 and server 106 each can be a device of the same or a different type from the electronic device 101. According to certain embodiments of this disclosure, the server 106 includes a group of one or more servers. Also, according to certain embodiments of this disclosure, all or some of the operations executed on the electronic device 101 can be executed on another or multiple other electronic devices (such as the electronic devices 102 and 104 or server 106). Further, according to certain embodiments of this disclosure, when the electronic device 101 should perform some function or service automatically or at a request, the electronic device 101, instead of executing the function or service on its own or additionally, can request another device (such as electronic devices 102 and 104 or server 106) to perform at least some functions associated therewith.

The other electronic device (such as electronic devices 102 and 104 or server 106) is able to execute the requested functions or additional functions and transfer a result of the execution to the electronic device 101. The electronic device 101 can provide a requested function or service by processing the received result as it is or additionally. To that end, a cloud computing, distributed computing, or client-server computing technique may be used, for example. While FIG. 1 shows that the electronic device 101 includes the communication interface 170 to communicate with the external electronic device 104 or server 106 via the network 162, the electronic device 101 may be independently operated without a separate communication function according to some embodiments of this disclosure.

The server 106 can include the same or similar components as the electronic device 101 (or a suitable subset thereof). The server 106 can support to drive the electronic device 101 by performing at least one of operations (or functions) implemented on the electronic device 101. For example, the server 106 can include a processing module or processor that may support the processor 120 implemented in the electronic device 101.

Although FIG. 1 illustrates one example of a network configuration 100 including an electronic device 101, various changes may be made to FIG. 1. For example, the network configuration 100 could include any suitable number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
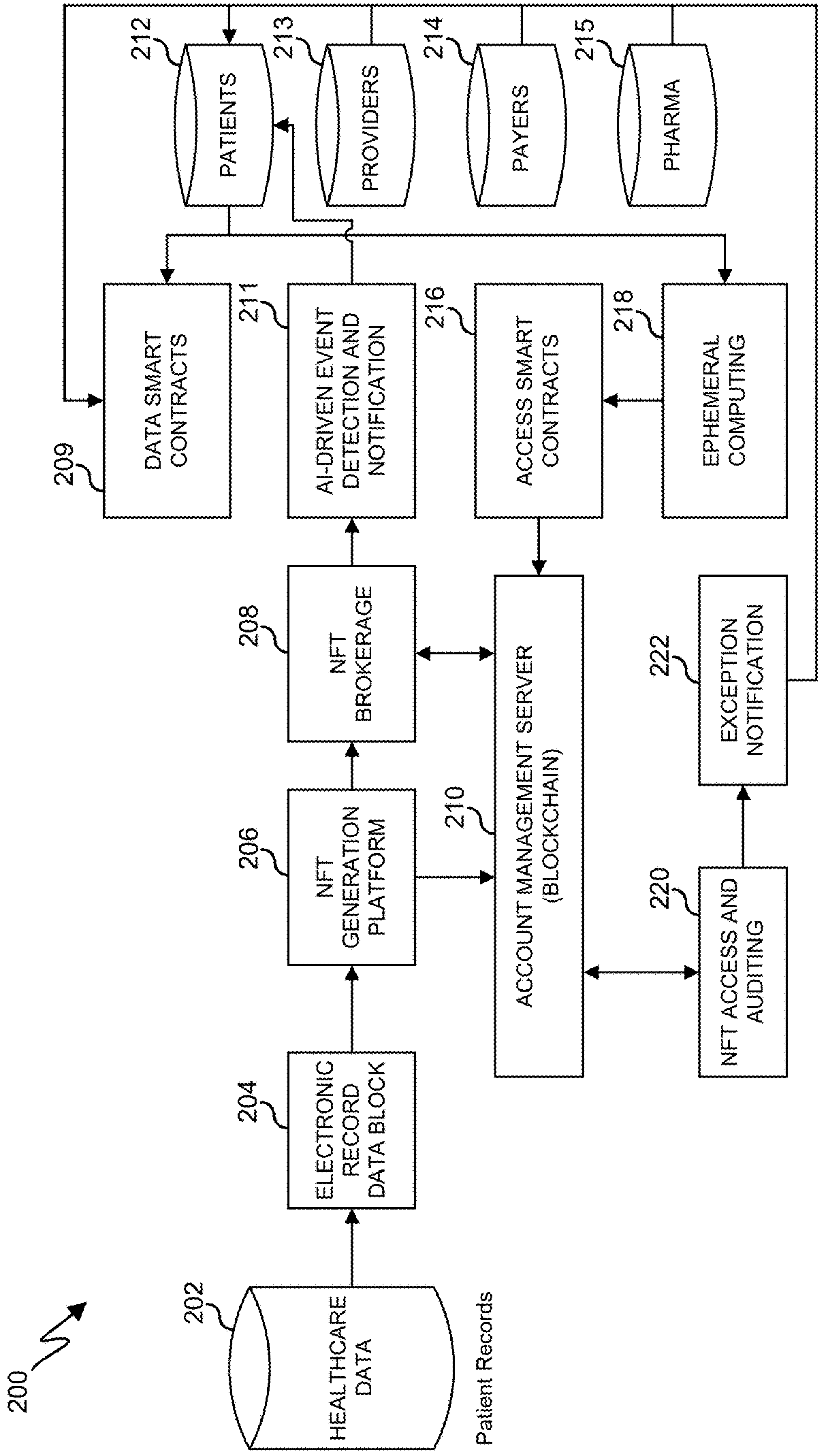
FIG. 2 illustrates an example contextual NFT generation system architecture in accordance with this disclosure.

FIG. 2 illustrates an example contextual NFT generation system architecture 200 in accordance with this disclosure. For ease of explanation, the architecture 200 shown in FIG. 2 is described as being implemented on or supported by the electronic device 101 in the network configuration 100 of FIG. 1. However, the architecture 200 shown in FIG. 2 could be used with any other suitable device(s) and in any other suitable system(s), such as when the architecture 200 is implemented on or supported by the server 106.

As shown in FIG. 2, the architecture 200 includes a healthcare database 202 that can include stored data representations and associations, such as patient healthcare data including patient financial records. The architecture 200 also includes an electronic record data block 204 that is a secure, encrypted, storage component that houses patient data obtained using the healthcare database 202, ensuring data integrity and privacy. The patient data in the electronic record data block 204 can include patient financial records. In various embodiments, AI-driven data preprocessing and standardization techniques can be employed to ensure data consistency and compatibility across different formats and sources of the patient data.

The architecture 200 also includes an NFT generation platform 206 that utilizes advanced machine learning techniques, such as natural language processing and machine learning algorithms, to analyze patient records in the electronic record data block 204 and generate contextual NFTs that represent the value and uniqueness of each record. The NFT generation platform ensures the secure creation, management, and transfer of NFTs among parties. The architecture 200 also includes an NFT brokerage that provides an intermediary service that facilitates the exchange of NFTs between parties, such as patients, healthcare providers, insurers, and other authorized parties. The NFT brokerage enables secure and efficient trading of NFTs representing access rights to patient records. The architecture 200 also includes an account management server 210 that incorporates a blockchain to provide a decentralized, tamper-proof ledger that manages patient financial records, NFT transactions, and access rights. The blockchain managed by the account management server 210 ensures transparency, trust, and immutability in the record-keeping process, facilitating collaboration among parties.

The architecture 200 also includes smart contracts 209 that are digitally enforced agreements that govern the terms and conditions for sharing patient financial records and exchanging NFTs. Smart contracts automate the execution of transactions and ensure compliance with privacy regulations and patient preferences. The architecture 200 also includes an AI-driven event detection and notification system 211 that utilizes advanced AI algorithms that are used to monitor NFT transactions and identify significant events or anomalies associated with the NFT construct. Patients and other parties can receive real-time notifications of these events, ensuring timely intervention and enhanced control.

The architecture 200 leverages advanced AI techniques and the blockchain to generate contextual NFTs to enable the creation, sharing, and tracking of patient record access among various parties. The NFT generation platform 206 records, transmits, and receives incentives, such as financial incentives, for granting access to financial records, and the electronic record data block 204 stores these records. In various embodiments, the account management server 210 is integrated with the NFT brokerage 208. The account management server 210 receives a record request associated with a user or party (e.g., a patient 212, a healthcare provider 213, a payer 214 of healthcare services for the patient, a pharmacy 215, and/or other users or parties) over the network (e.g., the network 162), queries the data store for a results set having records satisfying the query, generates a plurality of responses to the request as a function of the results set and state information associated with the network, and transmits the plurality of responses over the plurality of network interfaces, the plurality of responses being formatted for NFT protocols of the network to only share appropriate elements as approved by the patient/consumer as shareable and in a per-use fashion with an ability to get notified for any significant event associated with the NFT construct.

For example, when a user or party requests access to a record as governed by the data of the smart contracts 209, an access smart contracts operation 216 provides one or more queries to the account management server 210 including the requested information, so long as the requested information is allowed to be requested by the particular party under the smart contract. If so, the account management server 210 queries the data store for a results set having records satisfying the query, generates a plurality of responses to the request as a function of the results set and state information associated with the network, and transmits the plurality of responses over the plurality of network interfaces, the plurality of responses being formatted for NFT protocols of the network. Any access events can be communicated to the patient or other controlling party via the AI-driven event detection and notification system 211.

In some embodiments, as shown in FIG. 2, the architecture 200 can include an ephemeral computing operation 218 that can enforce and control smart contract access. For example, the ephemeral computing operation 218 can manage NFT access by allowing patients to grant access to their records for a specific duration or until certain conditions are met. The ephemeral computing operation 218 ensures that authorized parties can access the financial records only during the designated time frame or under the specified conditions, providing patients with enhanced control over their data. For example, in some embodiments, the architecture 200 supports expiration and revocation of NFT access rights, allowing patients or other controlling parties to terminate access to their records at any time. This feature ensures that patients or other controlling parties maintain full control over the sharing and accessibility of their sensitive information.

The architecture 200 also includes an NFT access and auditing operation 220 that tracks the access, usage, and sharing of NFTs, providing patients and other parties with visibility into how their records are being utilized. Any unauthorized access attempts or suspicious activities are flagged for review and appropriate action. For example, if an unauthorized access attempt or any suspicious activity is detected, this can be communicated to the party via the AI-driven event detection and notification system 211. In some embodiments, an exception notification 222 can be communicated to the patient or other controlling party.

In various embodiments, the architecture 200 can also include multi-factor authentication (MFA) operations to further secure access to NFTs and the associated records. The MFA operations can require users to present multiple forms of identification (e.g., passwords, biometric data, and/or security tokens) before granting access. In various embodiments, the architecture 200 can also include Role-Based Access Control (RBAC) in which the system employs role-based access control, ensuring that users only have access to NFTs and financial records relevant to their specific roles and responsibilities within the healthcare ecosystem. This feature enhances security by limiting unnecessary access to sensitive information.

In various embodiments, the architecture 200 can also include data fragmentation and encryption operations to protect the privacy of records. In various embodiments, the data fragmentation and encryption operations include the system fragmenting the data into smaller pieces and encrypting each piece separately before generating the NFT. This approach ensures that even if an unauthorized party gains access to the NFT, they cannot reconstruct the complete financial record without access to all the fragmented and encrypted data pieces. The architecture 200 also supports compliance with healthcare regulations, such as HIPAA, GDPR, and other data protection standards, ensuring that records and NFTs are managed, shared, and accessed in compliance with the relevant legal and ethical guidelines.

Although FIG. 2 illustrates one example of a contextual NFT generation system architecture 200, various changes may be made to FIG. 2. For example, various components and functions in FIG. 2 may be combined, further subdivided, replicated, or rearranged according to particular needs. Also, one or more additional components and functions may be included if needed or desired.

Figure 3:
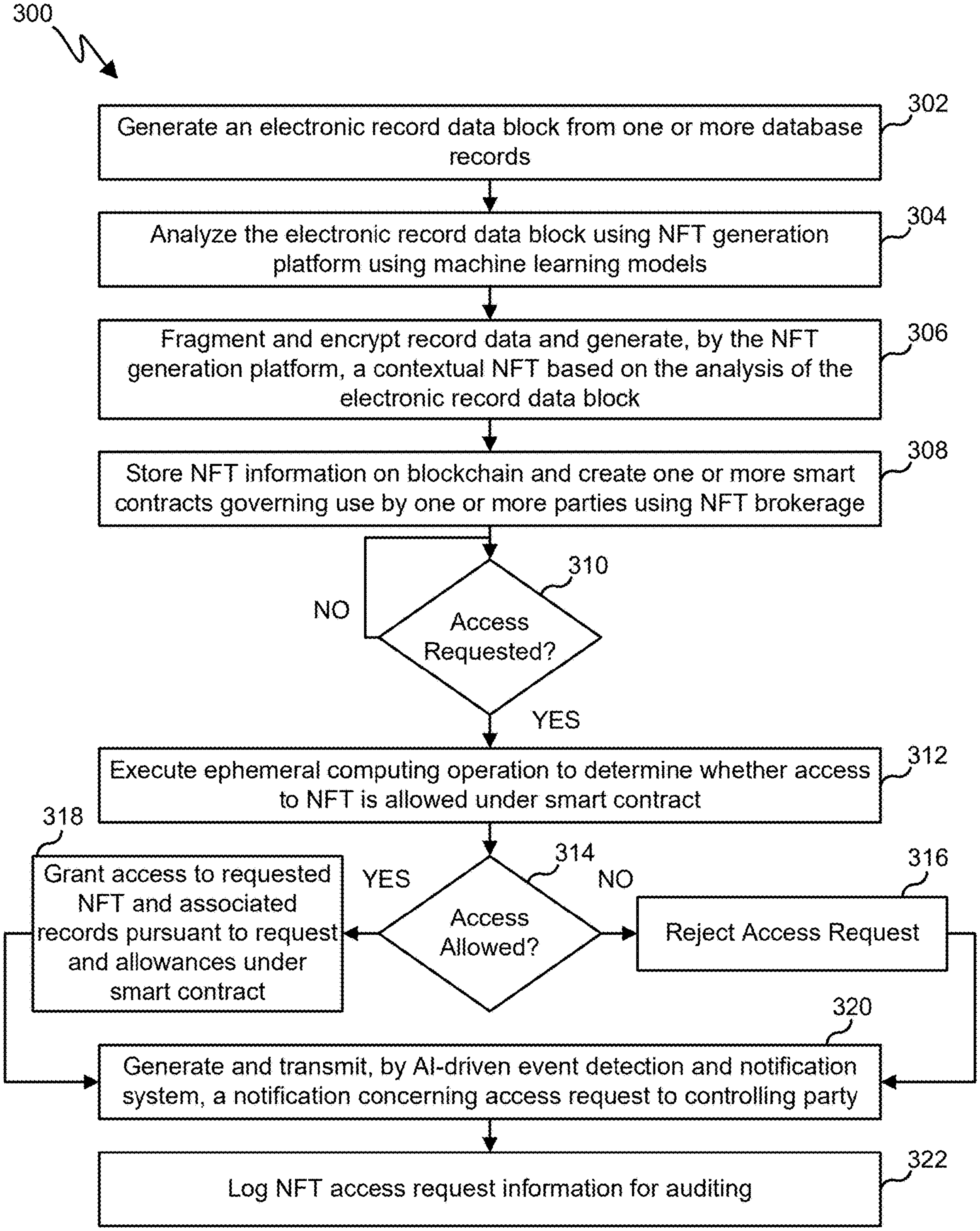
FIG. 3 illustrates an example method for contextual NFT generation and access control in accordance with this disclosure.

FIG. 3 illustrates an example method 300 for contextual NFT generation and access control in accordance with this disclosure. For ease of explanation, the method 300 shown in FIG. 3 is described as being performed using the electronic device 101 in the network configuration 100 of FIG. 1. However, the method 300 could be performed using any other suitable device(s), such as the server 106, and in any other suitable system(s).

At step 302, at least one processing device of the electronic device 101 generates an electronic record data block, e.g., the electronic record data block 204, from one or more database records, such as from the healthcare database 202. At step 304, the at least one processing device analyzes the electronic record data block via an NFT generation platform, e.g., the NFT generation platform 206. In various embodiments of this disclosure, the NFT generation platform is used to record, transmit, and receive incentives for granting access to records associated with the NFT. In various embodiments, the NFT generation platform includes machine learning models, such as one or more natural language processing models, that are used to analyze the data in the electronic record data block.

At step 306, the at least one processing generates, using the NFT generation platform, a contextual NFT based on the analysis of the electronic record data block. In various embodiments, before generation of the NFT, step 306 can include performing data fragmentation and encryption operations to protect the privacy of records. In various embodiments, the data fragmentation and encryption operations include the at least one processing device fragmenting the data into smaller pieces and encrypting each piece separately before generating the NFT. This approach ensures that even if an unauthorized party gains access to the NFT, they cannot reconstruct the complete record without access to all the fragmented and encrypted data pieces.

At step 308, the NFT information is stored on the blockchain and one or more smart contracts is created governing use of the NFT by one or more parties, such as by using an NFT brokerage system or service, such as the NFT brokerage 208. At step 310, it is determined whether access to the NFT and its associated records is requested. If not, the method 300 loops back to step 310. If so, the method 300 moves to step 312. The request can include a party, such as one of the parties 212-215, sending an access request that is received by the at least one processing device over a network. At step 312, one or more ephemeral computing operations, e.g., ephemeral computing operation(s) 218, are performed to determine whether access to the NFT is allowed under the smart contract. For example, the ephemeral computing operations enforce and control smart contract access. For instance, the ephemeral computing operations can manage NFT access by allowing patients or another NFT-controlling party to grant access to their records for a specific duration or until certain conditions are met. The ephemeral computing operations ensure that authorized parties can access the records only during the designated time frame or under the specified conditions, providing enhanced control over data.

At step 314, it is determined whether the requested access to the NFT and its associated records is allowed based on the party requesting access and their access permissions under the smart contract. If it is determined at step 314 that access is not allowed, then, at step 316, the access request is rejected and the requesting party can be notified of such a rejection. The method 300 then moves to step 320. If it is determined at step 314 that access is allowed, then, at step 318, the at least one processing device causes access to be granted to the NFT and its associated records pursuant to the nature of the request (e.g., the portions of the records requested) and pursuant to the allowances under the smart contract. The method 300 then moves to step 320.

At step 320, the at least one processing device generates and transmits, via an AI-driven event detection and notification system, e.g., the AI-driven event detection and notification system 211, a notification to the controlling party (e.g., a patient) of the NFT concerning the access request. For example, if the access request was denied at step 316, the notification can alert the controlling party that an unauthorized party attempted to access the NFT. If the access request was granted at step 318, the notification can alert the controlling party that an authorized party accessed the NFT, so that the controlling party can be made aware of how the NFT and the associated record information is being used, and by which parties it is being used. At step 322, the NFT access request information, such as including whether the request was denied or granted, the identity of the requesting party, the types of record information requested/accessed, etc., is logged for auditing, such as by the NFT access and auditing operation 220.

Although FIG. 3 illustrates one example of a method for contextual NFT generation and access control, various changes may be made to FIG. 3. For example, while shown as a series of steps, various steps in FIG. 3 could overlap, occur in parallel, occur in a different order, or occur any number of times (including zero times).

Figure 4:
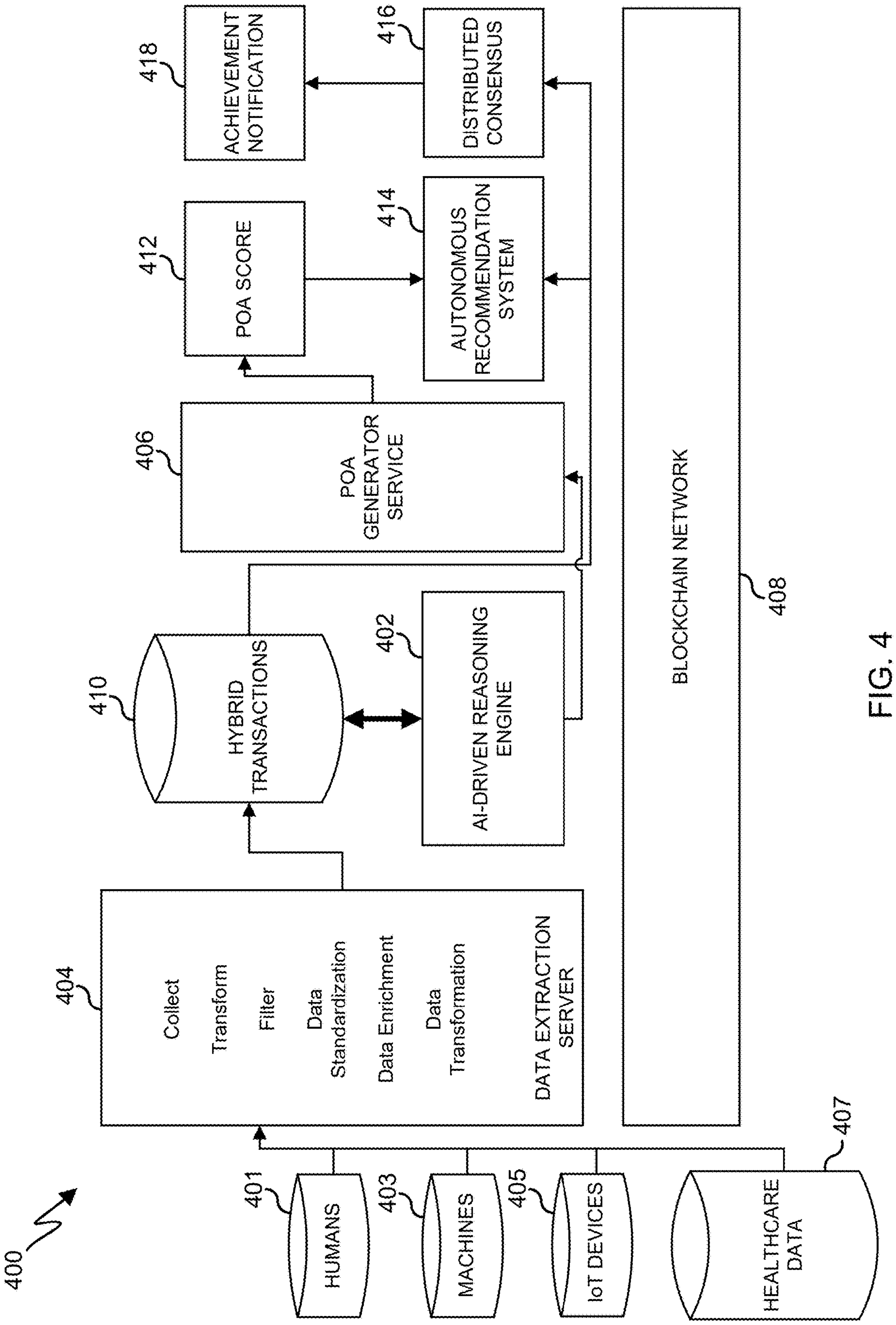
FIG. 4 illustrates an example hybrid proof of achievement architecture in accordance with this disclosure.

FIG. 4 illustrates an example hybrid proof of achievement architecture 400 in accordance with this disclosure. For ease of explanation, the architecture 400 shown in FIG. 4 is described as being implemented on or supported by the electronic device 101 in the network configuration 100 of FIG. 1. However, the architecture 400 shown in FIG. 4 could be used with any other suitable device(s) and in any other suitable system(s), such as when the architecture 400 is implemented on or supported by the server 106.

Distributed consensus algorithms form a cornerstones of blockchains. To build a good ecology of participants, autonomous recommendation of agreement is an important aspect of blockchain systems. Current enterprise solutions proof of achievement (POA) comes as a statistical output lacking an empirical nature. POA is aimed at arriving at a consensus by all interested parties exchanging the relevant activities. The architecture 400 provides an AI-powered distributed consensus system for hybrid (human and machine) transactions, focusing on rapidity, irreversibility, and agreement. This system aims to enhance the traditional POA approach by incorporating advanced AI techniques and enabling autonomous recommendation of agreement to foster a robust ecosystem of participants. The unique POA system of this disclosure involves all interested parties exchanging relevant activities, while a sophisticated reasoning engine facilitates the generation of a POA score, signifying relative achievement with respect to the original agreement or contract.

As shown in FIG. 4, the architecture 400 includes an AI driven reasoning engine 402, a data extraction server 404, a POA generator service 406, and a blockchain network 408. The data extraction server 404 can be connected to various data sources including human sources 401, machine sources 403, IoT sources 405, and healthcare data sources 407. The data sources may have their data stored in the form of databases. The data extraction server 404 can be a dedicated server responsible for extracting relevant data from various sources involved in hybrid transactions. The data extraction server supports seamless integration with human and machine participants, such as smart contracts, IoT devices, and automated systems, to collect and preprocess data required for the AI-driven reasoning engine. The data extraction server 404, using the various data sources, collects, transforms and/or filters the data, and/or performs data standardization, data enrichment, and/or data transformation on the data. For example, the data extraction server performs data acquisition and normalization by collecting data from the multiple sources and performs data preprocessing techniques such as data cleaning, transformation, and normalization to ensure a consistent format and representation across different sources.

In various embodiments, data collection performed by the data extraction server 404 involves the data extraction server 404 connecting to various data sources, such as databases, APIs, IoT devices, and third-party services, to collect the necessary data related to the hybrid transactions. In various embodiments, data transformation performed by the data extraction server 404 involves the data extraction server 404 transforming the collected data into a unified format compatible with the AI-driven reasoning engine 402. This can include parsing, decoding, and converting data to ensure seamless integration with the rest of the system.

In various embodiments, data filtering performed by the data extraction server 404 involves the data extraction server 404 filtering the collected data based on predefined criteria or rules, ensuring that only relevant and high-quality data is passed on to the AI-driven reasoning engine for further analysis. In various embodiments. data enrichment performed by the data extraction server 404 involves the data extraction server 404 enriching the collected data with additional information from external sources, if required, to enhance the context and accuracy of the data fed into the AI-driven reasoning engine. In various embodiments, data transmission performed by the data extraction server 404 involves the data extraction server 404 securely transmitting the preprocessed data to the AI-driven reasoning engine 402 for further analysis, feature extraction, and POA score calculation.

The processed data can be securely stored on the blockchain network 408, ensuring data integrity, immutability, and traceability. The preprocessed data can be stored in or used by a hybrid transactions data store or hybrid transactions operation 410. The hybrid transactions are transactions involving both human and machine participants, such as smart contracts, IoT devices, and automated systems, in a blockchain-based ecosystem.

The AI-driven reasoning engine 402 is an advanced AI component of the architecture 400 that processes the data from the relevant activities exchanged by the interested parties. The AI-driven reasoning engine 402 employs machine learning algorithms, natural language processing, and pattern recognition techniques to analyze the data and derive meaningful insights and facilitate the consensus process in a transparent and explainable manner. The AI-driven reasoning engine 402 is responsible for processing and analyzing the data from relevant activities exchanged by interested parties, ultimately generating a POA score for each participant.

In various embodiments, the reasoning engine 402 can perform data preprocessing such as employing data preprocessing techniques to clean, normalize, and standardize the data from relevant activities, ensuring consistency and compatibility across different formats and sources, and improving the accuracy and efficiency of subsequent analysis.

In various embodiments, additionally or alternatively, the reasoning engine 402 can perform feature extraction by using natural language processing and pattern recognition techniques, to identify and extract relevant features and variables from the preprocessed data. These features represent aspects of the relevant activities and serve as input for machine learning operations.

In various embodiments, additionally or alternatively, the reasoning engine 402 can perform machine learning operations such that the reasoning engine leverages various machine learning techniques, such as supervised learning, unsupervised learning, and reinforcement learning, to analyze the extracted features and identify patterns, correlations, and trends. These algorithms adapt and improve over time as new data is introduced, enhancing the overall performance of the reasoning engine.

In various embodiments, additionally or alternatively, the reasoning engine 402 can perform knowledge representation and reasoning operations in which the reasoning engine 402 utilizes knowledge representation techniques, such as ontologies, semantic networks, and rule-based systems, to store and organize the acquired knowledge. This structured knowledge base enables the engine 402 to reason and infer new insights based on the existing information.

In various embodiments, additionally or alternatively, the reasoning engine 402 can perform, such as in conjunction with the POA generator service 406, a POA score calculation. The AI-driven reasoning engine 402 and the POA generation service 406 can be seamlessly integrated into the blockchain network 408, ensuring secure and transparent record-keeping of hybrid transactions and the resulting POA scores. The reasoning engine 402 computes a POA score 412 for each participant by evaluating their performance concerning the original agreement or contract. The calculation takes into account various factors, such as the relevance, quality, and timeliness of the activities exchanged, as well as any predefined performance metrics or benchmarks. The POA generator service 406 can be a specialized service responsible for calculating and assigning POA scores to the participants of hybrid transactions. The POA generator service 406 interacts with the AI-driven reasoning engine 402, leveraging its analytical capabilities and knowledge base to derive meaningful insights and generate accurate POA scores for each participant.

In various embodiments, the POA generator service 406 can perform POA score request handling in which the service receives and processes requests for POA score calculation from the participants of hybrid transactions or the system itself. In various embodiments, the POA generator service 406 can interact with the AI-driven reasoning engine 402, such as by communicating with the AI-driven reasoning engine 402 and requesting analysis, insights, and evaluations required for POA score calculation.

In various embodiments, the POA generator service 406 can perform at least a part of the POA score calculation based on the information received from the AI-driven reasoning engine 402, in which the POA generator service 406 computes the POA score 412 for each participant, taking into account various factors such as relevance, quality, timeliness of the activities exchanged, and any predefined performance metrics or benchmarks.

In various embodiments, the POA generator service 406 can perform POA score assignment in which the POA generator service 406 assigns the calculated POA scores to the respective participants, updating their records within the blockchain network 408 and a distributed consensus operation 416.

In various embodiments, the POA generator service 406 can perform POA score reporting in which the POA generator service 406 generates and delivers reports on the POA scores 412 to the relevant parties, such as participants, regulators, and system administrators. The reports provide insights into the participants' performance and achievement in fulfilling the original agreement or contract, promoting transparency and accountability within the hybrid transaction ecosystem.

In various embodiments, the POA generator service 406 can perform continuous improvement in which the POA generation service 406 monitors and evaluates the accuracy and effectiveness of the POA scores 412, collecting feedback from the parties and providing it to the AI-driven reasoning engine for further refinement and improvement of the operations and knowledge base of the architecture 400.

In various embodiments, additionally or alternatively, the reasoning engine 402 can perform continuous learning and improvement operations in which the AI-driven reasoning engine 402 continuously learns from new data and feedback, refining its machine learning models and updating the knowledge base to ensure the most accurate and up-to-date POA scores. This dynamic learning process enables the system to adapt to evolving requirements and conditions in the hybrid transaction ecosystem.

In various embodiments, additionally or alternatively, the reasoning engine 402 can provide explainability and interpretability. That is, the reasoning engine 402 is designed to provide explainable and interpretable results, allowing parties to understand the rationale behind the generated POA scores. This transparency is crucial for building trust and confidence in the system, as well as facilitating the consensus process among participants.

In various embodiments, the POA generator service 406 works with the AI-driven reasoning engine to calculate the POA score 412 for each participant, representing their relative achievement in fulfilling the terms and conditions of the original agreement or contract, which is passed to an autonomous recommendation system 414. The autonomous recommendation system 414 is an AI-powered mechanism that autonomously recommends agreements based on the POA scores, fostering a self-sustaining ecosystem of participants and encouraging continuous improvement in performance. The architecture 400 also includes the distributed consensus operation 416 that uses a decentralized protocol that leverages the AI-driven reasoning engine and the POA scores to achieve consensus among the participants in the hybrid transactions. An achievement notification 418 can then be transmitted to one or more parties.

Although FIG. 4 illustrates one example of a hybrid proof of achievement architecture 400, various changes may be made to FIG. 4. For example, various components and functions in FIG. 4 may be combined, further subdivided, replicated, or rearranged according to particular needs. Also, one or more additional components and functions may be included if needed or desired.

Figure 5:
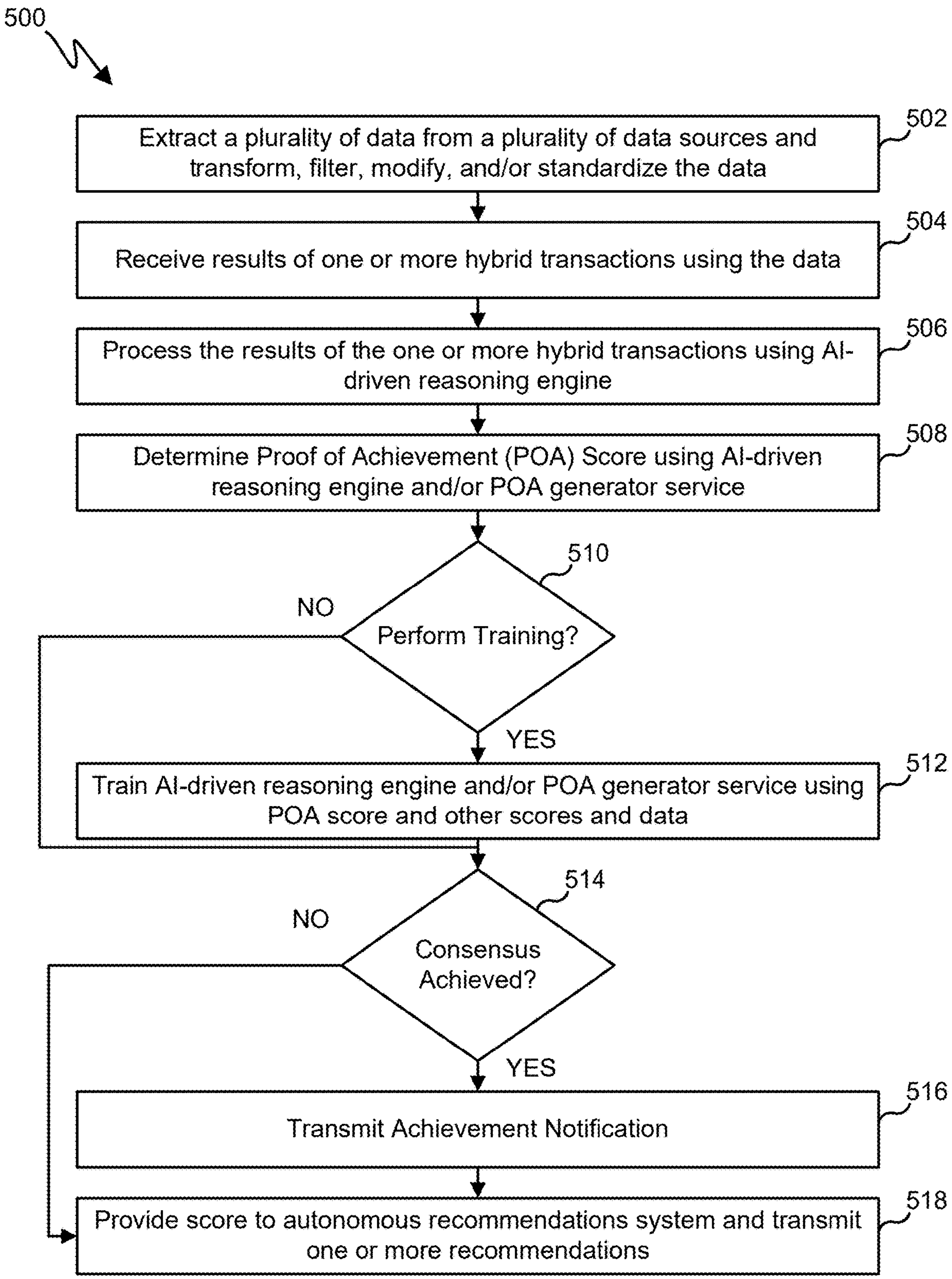
FIG. 5 illustrates an example method for hybrid proof of achievement in accordance with this disclosure.

FIG. 5 illustrates an example method 500 for hybrid proof of achievement in accordance with this disclosure. For ease of explanation, the method 500 shown in FIG. 5 is described as being performed using the electronic device 101 in the network configuration 100 of FIG. 1. However, the method 500 could be performed using any other suitable device(s), such as the server 106, and in any other suitable system(s).

At step 502, at least one processing device extracts a plurality of data from a plurality of data sources and transforms, filters, modifies, and/or standardizes the data. For example, as described with respect to FIG. 4, the data extraction server 404 can be used to extract the data from sources such as the sources 401, 403, 405, 407 and perform the manipulation of the data. At step 504, the at least one processing device receives results of one or more hybrid (i.e., human and machine) transactions using the data.

At step 506, the at least one processing device processes the results of the one or more hybrid transactions are processed using an AI-driven reasoning engine, such as the engine 402. As also described with respect to FIG. 4, the AI-driven reasoning engine 402 is an advanced AI component that processes the data from the relevant activities exchanged by interested parties. The AI-driven reasoning engine employs machine learning algorithms, natural language processing, and pattern recognition techniques to analyze the data and derive meaningful insights and facilitate the consensus process in a transparent and explainable manner. In various embodiments, the reasoning engine can perform data preprocessing such as employing data preprocessing techniques to clean, normalize, and standardize the data from relevant activities, ensuring consistency and compatibility across different formats and sources, and improving the accuracy and efficiency of subsequent analysis.

In various embodiments, additionally or alternatively, the reasoning engine can perform feature extraction by using natural language processing and pattern recognition techniques, to identify and extract relevant features and variables from the preprocessed data. These features represent aspects of the relevant activities and serve as input for machine learning operations. In various embodiments, additionally or alternatively, the reasoning engine can perform knowledge representation and reasoning operations in which the reasoning engine utilizes knowledge representation techniques, such as ontologies, semantic networks, and rule-based systems, to store and organize the acquired knowledge. This structured knowledge base enables the engine to reason and infer new insights based on the existing information.

At step 508, the at least one processing device determines a POA score using the AI-driven reasoning engine and/or a POA generator service, such as the POA generator service 406. The reasoning engine is responsible for processing and analyzing the data from relevant activities exchanged by interested parties, ultimately generating a POA score for each participant. In some embodiments, the POA generator service can be part of the AI-driven reasoning engine. The AI-driven reasoning engine and the POA generation service can be seamlessly integrated into a blockchain network, such as the blockchain network 408, ensuring secure and transparent record-keeping of hybrid transactions and the resulting POA scores. The reasoning engine computes a POA score for each participant by evaluating their performance concerning the original agreement or contract. The calculation takes into account various factors, such as the relevance, quality, and timeliness of the activities exchanged, as well as any predefined performance metrics or benchmarks. The POA generator service can be a specialized service responsible for calculating and assigning POA scores to the participants of hybrid transactions. The POA generator service can interact with the AI-driven reasoning engine, leveraging its analytical capabilities and knowledge base to derive meaningful insights and generate accurate POA scores for each participant.

At step 510, it is determined whether to train the reasoning engine and/or the POA generator service. For example, in various embodiments, the reasoning engine can perform machine learning operations such that the reasoning engine leverages various machine learning techniques, such as supervised learning, unsupervised learning, and reinforcement learning, to analyze the extracted features and identify patterns, correlations, and trends. These algorithms can be adapted and improved over time via training as new data is introduced, enhancing the overall performance of the reasoning engine. In various embodiments, the POA generator service can perform continuous improvement in which the POA generation service monitors and evaluates the accuracy and effectiveness of the POA scores, collecting feedback from the parties and providing it to the AI-driven reasoning engine for further refinement and improvement of system operations and knowledge bases.

If, at step 510, it is determined that training is not to be performed, the method 500 moves to step 514. If, at step 510, it is determined that training is to be performed, the method 500 moves to step 512, at which the reasoning engine and/or the POA generator service are trained using the POA score generated at step 508, and other scores and data, such as ground truth data received at the system via a training feedback loop. The method 500 then moves to step 514.

At step 514, it is determined whether consensus is achieved. That is, the method can include obtaining a distributed consensus, such as via distributed consensus operation 416, that uses a decentralized protocol that leverages the AI-driven reasoning engine and the POA scores to achieve consensus among the participants in the hybrid transactions. If consensus is not achieved, the method 500 moves to step 518. If consensus is achieved, then, at step 516, in various embodiments, an achievement notification can be transmitted to one or more parties. At step 518, the at least one processing device causes the score to be provided to an autonomous recommendations system (e.g., the autonomous recommendations system 414) which transmits one or more recommendations. For example, the autonomous recommendation system is an AI-powered mechanism that autonomously recommends agreements based on the POA scores, fostering a self-sustaining ecosystem of participants and encouraging continuous improvement in performance.

Although FIG. 5 illustrates one example of a method 500 for hybrid proof of achievement, various changes may be made to FIG. 5. For example, while shown as a series of steps, various steps in FIG. 5 could overlap, occur in parallel, occur in a different order, or occur any number of times (including zero times).

Figure 6:
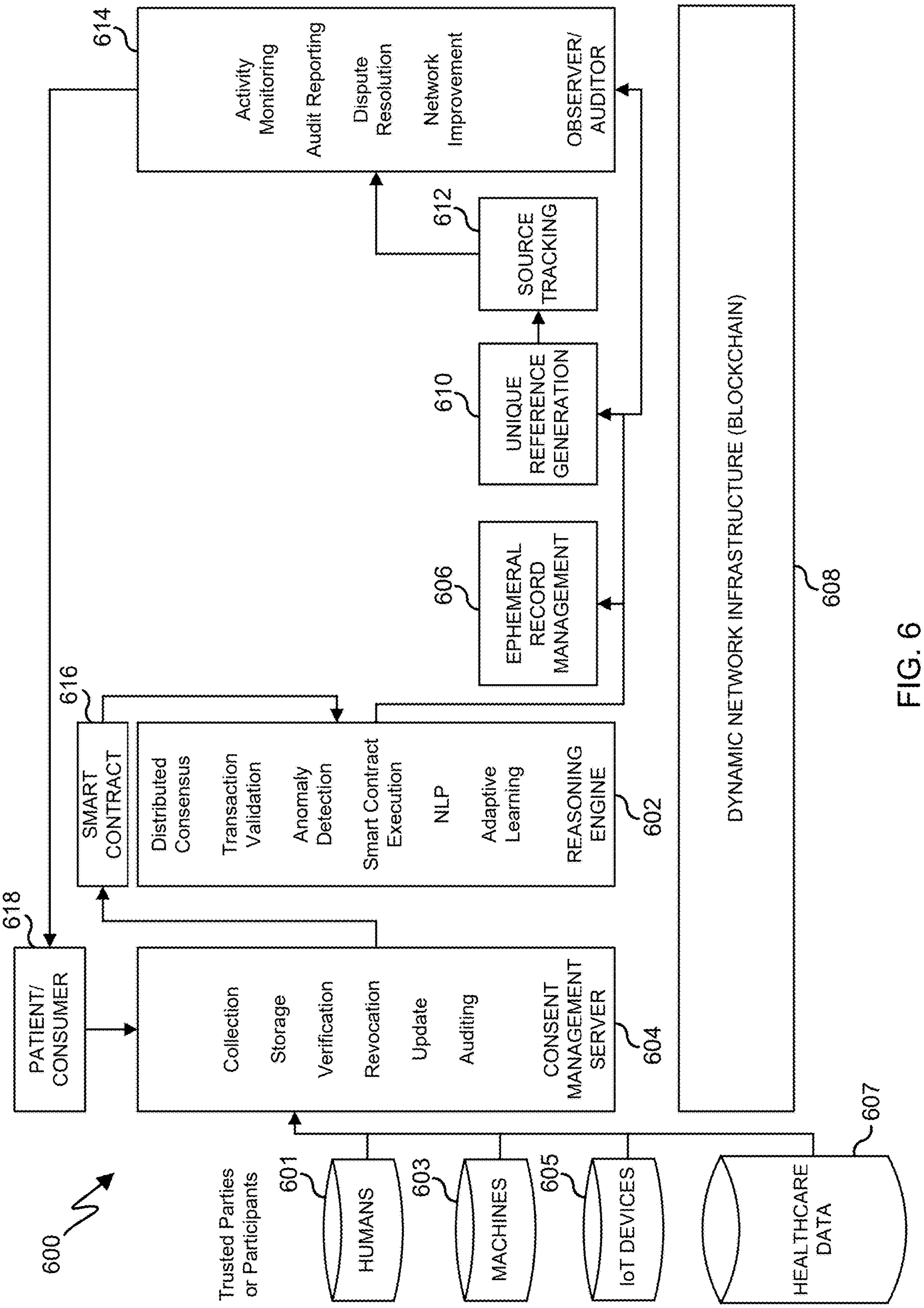
FIG. 6 illustrates an example architecture for a dynamic network for trusted information exchange in accordance with this disclosure.

FIG. 6 illustrates an example architecture 600 for a dynamic network for trusted information exchange in accordance with this disclosure. For ease of explanation, the architecture 600 shown in FIG. 6 is described as being implemented on or supported by the electronic device 101 in the network configuration 100 of FIG. 1. However, the architecture 600 shown in FIG. 6 could be used with any other suitable device(s) and in any other suitable system(s), such as when the architecture 600 is implemented on or supported by the server 106.

As shown in FIG. 6, the architecture 600 includes a reasoning engine 602, which can also the reasoning engine 402 in various embodiments, a consent management server 604, an ephemeral record management system 606, and a dynamic network infrastructure 608. The reasoning engine 602 uses advanced AI techniques to enable transparent and efficient information sharing while ensuring data privacy and security. The ephemeral record management system 606 includes an infrastructure that deletes sensitive data from local storage of recipients after a specific duration and/or confirmation event, replacing the deleted record with a unique reference pointer using a unique reference generation system 610 to the original timestamped source for legal and reference purposes. The original timestamped source is used by a source tracking operation 612 to track all unique references to the original recipient. Additionally, in various embodiments, the authority of the network can add an observer/auditor 614 to the unique reference in consensus with two or more authorities in a multi-authority POA network. The observer/auditor 614 can provide information to parties such as a patient/consumer 618.

The reasoning engine 602 interacts with the consent management server 604 via smart contracts 616. The consent management server 604 can be a dedicated server within the architecture 600 that is responsible for managing and enforcing consumer consent. The consent management server interacts with the dynamic network infrastructure 608, smart contracts 616, and AI-driven event detection systems of the reasoning engine 602 to ensure that sensitive information is shared only with authorized parties and in compliance with consumer preferences.

The architecture 600 uses consent management in which the architecture 600 prioritizes consumer consent by incorporating smart contracts and AI-driven event detection to ensure that sensitive information is only shared with authorized parties and in accordance with consumer preferences. The consent management server 604 is configured to perform consent collection, in which the server collects and records consent from sources for the sharing of sensitive information, ensuring that data is only shared with authorized parties and for specific purposes. These sources can include human sources 601, machine sources 603, IoT device sources 605, and healthcare data sources 607. The consent management server 604 is also configured to perform consent storage, in which the consent management server 604 securely stores consent records, using encryption and other security measures to protect the data from unauthorized access or manipulation. The consent management server 604 is also configured to perform consent verification, in which the server verifies consumer consent before allowing the exchange of sensitive information between trusted parties, ensuring compliance with consumer preferences and legal requirements. The consent management server 604 is also configured to perform consent revocation, in which the consent management server 604 enables consumers to revoke their consent at any time, providing them with control over their sensitive information and its usage.

The consent management server 604 is also configured to perform consent updating, in which the consent management server 604 allows consumers to update their consent preferences, ensuring that their choices are accurately reflected in the system. The consent management server 604 is also configured to perform consent auditing, in which the consent management server 604 maintains a comprehensive audit trail of all consent-related activities, including the collection, storage, verification, revocation, and updating of consent records. This audit trail enables traceability and accountability, ensuring compliance with regulations and consumer consent requirements. The consent management server 604 is also configured to perform observer/auditor integration. In multi-authority POA networks of this disclosure, the observer/auditor 614 serves as an independent, neutral party responsible for monitoring and overseeing the activities within the network. The authority can add an observer/auditor 614 to the unique reference in consensus with two or more authorities, enhancing the transparency and oversight of the network.

The dynamic network infrastructure 608 includes blockchain technology to create a decentralized, secure, and transparent network for trusted parties to exchange sensitive information with consumer consent. The dynamic nature of the network enables seamless onboarding and offboarding of participants, ensuring efficient collaboration.

The architecture 600 utilizes an AI-powered distributed consensus in which the system incorporates the advanced AI-driven reasoning engine 602 to facilitate distributed consensus among network participants. The engine 602 uses machine learning algorithms, natural language processing, and pattern recognition techniques to analyze relevant activities, validate transactions, and reach consensus efficiently and securely. In some embodiments, the system can manage sensitive information through ephemeral records that are automatically deleted from the recipient's local storage after a specific duration or confirmation event. This approach ensures data privacy while maintaining a record of the transaction for legal and reference purposes. The ephemeral record management system 606 ensures data privacy, security, and compliance with consumer consent while maintaining traceability and accountability in the information exchange process. The ephemeral record management system 606 utilizes the temporary storage and automatic deletion of sensitive information from a recipient's local storage after a specific duration or confirmation event. This approach addresses the challenges associated with long-term storage of sensitive data and minimizes the risk of unauthorized access or data breaches. The ephemeral record management uses an ephemeral record infrastructure that deletes sensitive data from the local storage of the recipient after a specific duration and/or a confirmation event. The deleted record is replaced with a unique reference pointer via the unique reference generation system 610 to an original timestamped source for legal and reference purposes. The source tracking operation 612 tracks all unique references to the original recipient. The authority of the network can add an observer/auditor 614 to the unique reference in consensus with two or more authorities in a multi-authority POA network.

In various embodiments, the ephemeral record management system 606 enforces temporary storage in which, upon receiving sensitive information, the recipient's local storage maintains the data temporarily. The duration of storage can be predefined by the sender or the network, based on the nature of the information, consumer consent, and legal requirements. In various embodiments, the ephemeral record management system 606 also enforces auto-deletion in which the system automatically deletes the sensitive data from the recipient's local storage after a specified duration or upon the occurrence of a confirmation event. This event can be an acknowledgment from the recipient, completion of a specific task or transaction, or any other predefined trigger agreed upon by the involved parties. In various embodiments, the ephemeral record management system 606 also uses the unique reference pointer in which, when the ephemeral record is deleted, the system generates a unique reference pointer to the original timestamped source of the data using the unique reference generation system 610. This pointer enables participants to access the information for legal and reference purposes without storing the sensitive data locally.

In various embodiments, the ephemeral record management system 606 also enforces data encryption. To further enhance data security, the ephemeral record management system 606 can incorporate advanced encryption techniques to protect sensitive information during transmission and storage. This ensures that even if unauthorized access occurs, the data remains unintelligible to malicious actors. In various embodiments, the ephemeral record management system 606 also uses audit trails in which the system maintains a comprehensive audit trail of all activities associated with the ephemeral records, including the creation, access, deletion, and unique reference generation. This audit trail enables traceability and accountability, ensuring compliance with regulations and consumer consent requirements. In various embodiments, the ephemeral record management system 606 also enforces access control in which the ephemeral record management system 606 implements robust access control mechanisms to ensure that only authorized parties can access the sensitive information. This can include authentication, authorization, and role-based access control, as well as the integration of blockchain-based identity management systems.

In various embodiments, the ephemeral record management system 606 also enforces data recovery and backup. In case of system failures or data corruption, the ephemeral record management system 606 can incorporate data recovery and backup mechanisms, allowing the restoration of critical information without compromising data privacy and security. By integrating these elements and functionalities, the ephemeral record management system 606 provides a secure, efficient, and privacy-preserving solution for managing sensitive information in the network. The system allows trusted parties to exchange data with consumer consent while minimizing the risk of unauthorized access or data breaches, promoting transparency and trust among network participants.

The unique reference generation system 610, upon deletion of an ephemeral record, generates a unique reference pointer to the original timestamped source, allowing participants to access the information for legal and reference purposes without storing the sensitive data locally. Unique reference generation ensures traceability, accountability, and compliance with consumer consent and legal requirements, while maintaining data privacy and security. The unique reference is generated when an ephemeral record is deleted from a recipient's local storage, serving as a pointer to the original timestamped source of the data. This enables participants to access the information for legal and reference purposes without the need for storing the sensitive data locally. The unique reference identifier that points to the original timestamped source of the data can be a hash value, a combination of alphanumeric characters, or any other unique representation that ensures the data's traceability.

The unique reference generation system 610 also performs timestamping in which the unique reference generation system 610 includes a timestamp for each reference, indicating the exact time and date when the reference was created. This provides a chronological context for the data access and deletion events, which is crucial for legal and reference purposes. The unique reference generation system 610 also performs metadata storage in which the system 610 stores metadata associated with the unique reference, such as the sender, recipient, data type, and purpose of the data exchange. This metadata helps provide context for the reference and facilitates traceability and accountability.

The unique reference generation system 610 also performs data access control in which the unique reference generation system 610 incorporates robust access control mechanisms to ensure that only authorized parties can access the original timestamped source of the data. This can include authentication, authorization, and role-based access control, as well as integration with blockchain-based identity management systems. The unique reference generation system 610 also performs reference validation in which the system 610 includes a validation mechanism to verify the authenticity and integrity of the unique reference. This can be achieved using cryptographic techniques, such as digital signatures and hash functions, ensuring that the reference has not been tampered with or altered.

The unique reference generation system 610 also uses an immutable record. The unique reference and its associated metadata are stored on a blockchain or another immutable data structure, ensuring the data's integrity and preventing unauthorized modifications. The unique reference generation system 610 also performs reference expiration. In some cases, the unique reference may have an expiration date or condition, after which the reference becomes invalid or inaccessible. This can be useful for compliance with data retention policies or specific legal requirements. By incorporating these elements and functionalities, the unique reference generation system 610 ensures that sensitive data remains secure and private while maintaining traceability, accountability, and compliance with consumer consent and legal requirements. The system enables participants to access necessary information for legal and reference purposes without exposing the sensitive data to potential security risks or breaches.

The observer/auditor 614 monitors the exchange of sensitive information within the network, ensuring that data sharing is in compliance with consumer consent and legal requirements. The observer/auditor 614 also performs compliance verification in which the observer/auditor verifies that the network's activities are in accordance with applicable regulations, including data privacy, security, and consumer protection laws. The observer/auditor 614 also performs audit reporting in which the observer/auditor 614 generates and delivers audit reports to relevant parties, such as network participants, authorities, and regulators, providing insights into the network's activities and compliance status. The observer/auditor 614 also performs dispute resolution in which the observer/auditor 614 may play a role, offering an unbiased perspective and assisting in the resolution of disagreements between network participants. The observer/auditor 614 also performs network improvement in which the observer/auditor provides feedback to the network authority and other parties, helping identify areas for improvement and promoting the continuous enhancement of the system.

The reasoning engine 602 is responsible for facilitating AI-driven distributed consensus, transaction validation, and decision-making within the network. It leverages advanced AI techniques, such as machine learning, natural language processing, and pattern recognition, to analyze and process relevant activities, ensuring efficient and secure operation. The reasoning engine 602 can perform distributed consensus in which the reasoning server employs AI-driven algorithms to facilitate consensus among network participants, ensuring that transactions and data sharing are agreed upon by a majority of the participants. This consensus process enhances the security, transparency, and trust within the network.

The reasoning engine 602 can also perform transaction validation in which the server uses AI techniques to validate transactions within the network, ensuring that they are legitimate, compliant with consumer consent, and adhere to predefined network rules. By validating transactions, the reasoning server 602 helps maintain the integrity and reliability of the network. The reasoning engine 602 can also perform anomaly detection in which the reasoning server 602 is capable of detecting anomalies and potential fraudulent activities within the network. It uses machine learning algorithms to identify unusual patterns, irregularities, or deviations from the norm, alerting relevant parties to take necessary action.

The reasoning engine 602 can also perform smart contract execution in which the server is responsible for executing smart contracts within the network, automating various processes and agreements among participants. It ensures that smart contracts are executed accurately and in accordance with their predefined conditions. The reasoning engine 602 can also perform decision support in which the reasoning server 602 provides decision support to network participants by offering insights, recommendations, and guidance based on the analysis of historical data, patterns, and trends. This can help participants make more informed decisions, optimize processes, and enhance overall network efficiency.

The reasoning engine 602 can also perform natural language processing (NLP) in which the engine 602 leverages NLP techniques to understand and interpret textual data within the network, such as user input, contractual agreements, and communication among participants. This enables the system to process and analyze unstructured data, enhancing its decision-making capabilities. The reasoning engine 602 can also perform adaptive learning in which the reasoning engine 602 continually learns from its interactions and experiences within the network, improving its algorithms and decision-making capabilities over time. This adaptive learning feature allows the server to stay up-to-date with the evolving needs and requirements of the network and its participants.

The reasoning engine 602 can also perform data privacy preservation in which the engine 602 is designed to ensure data privacy by incorporating advanced encryption techniques and privacy-preserving algorithms. This ensures that sensitive information remains protected during processing and analysis, minimizing the risk of unauthorized access or data breaches.

The architecture 600 thus provides an AI-powered distributed consensus system for secure, monitored, and automated exchange of sensitive information between trusted parties, all with consumer consent. This system allows for distributed consensus, monitoring, and automatic exchange of sensitive information between trusted parties for the purposes of an activity.

Although FIG. 6 illustrates one example of an architecture 600 for a dynamic network for trusted information exchange, various changes may be made to FIG. 6. For example, various components and functions in FIG. 6 may be combined, further subdivided, replicated, or rearranged according to particular needs. Also, one or more additional components and functions may be included if needed or desired.

Figure 7:
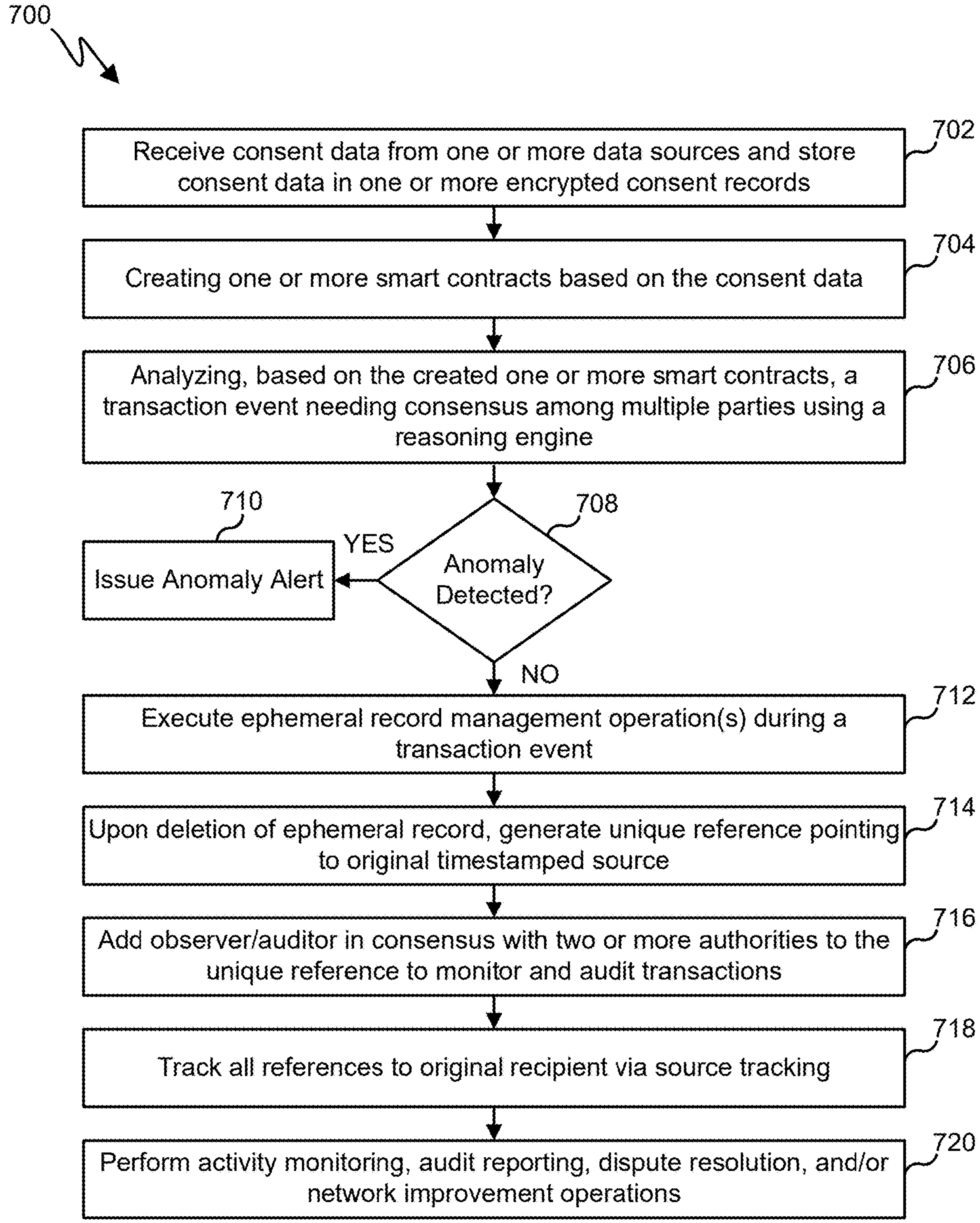
FIG. 7 illustrates an example method for a dynamic network for trusted information exchange in accordance with this disclosure.

FIG. 7 illustrates an example method 700 for a dynamic network for trusted information exchange in accordance with this disclosure. For ease of explanation, the method 700 shown in FIG. 7 is described as being performed using the electronic device 101 in the network configuration 100 of FIG. 1. However, the method 700 could be performed using any other suitable device(s), such as the server 106, and in any other suitable system(s).

At step 702, content data is received from one or more data sources and stored in one or more encrypted records. For example, as described with respect to FIG. 6, the consent management server 604 can receive the consent data from sources such as the sources 601, 603, 605, 607, in which the server collects and records consent from the sources for the sharing of sensitive information, ensuring that data is only shared with authorized parties and for specific purposes. The consent management server can also perform consent verification, in which the server verifies consumer consent before allowing the exchange of sensitive information between trusted parties, ensuring compliance with consumer preferences and legal requirements, and/or consent revocation, in which the consent management server enables consumers to revoke their consent at any time, providing them with control over their sensitive information and its usage. The consent management server is also configured to perform consent updating, in which the consent management server allows consumers to update their consent preferences, ensuring that their choices are accurately reflected in the system.

The consent management server is also configured to perform consent auditing, in which the consent management server maintains a comprehensive audit trail of all consent-related activities, including the collection, storage, verification, revocation, and updating of consent records. This audit trail enables traceability and accountability, ensuring compliance with regulations and consumer consent requirements. The consent management server is also configured to perform observer/auditor integration. In multi-authority POA networks of this disclosure, the observer/auditor serves as an independent, neutral party responsible for monitoring and overseeing the activities within the network. The authority can add an observer/auditor to the unique reference in consensus with two or more authorities, enhancing the transparency and oversight of the network.

At step 704, one or more smart contracts are created based on the consent data. The smart contracts can be used by a reasoning engine such as the reasoning engine 602 described with respect to FIG. 6. The one or more smart contracts are used by the reasoning engine to interact with the consent management server to enforce consent preferences and ensure sensitive is shared only with authorized parties and in compliance with consumer preferences. At step 706, a transaction event needing consensus among multiple parties is analyzed using the reasoning engine based on the created one or more smart contracts.

The reasoning engine can leverage advanced AI techniques, such as machine learning, natural language processing, and pattern recognition, to analyze and process relevant activities, ensuring efficient and secure operation. The reasoning engine performs distributed consensus in which the reasoning engine employs AI-driven algorithms to facilitate consensus among network participants, ensuring that transactions and data sharing are agreed upon by a majority of the participants based on the one or more smart contracts. This consensus process enhances the security, transparency, and trust within the network. The reasoning engine ensures that smart contracts are executed accurately and in accordance with their predefined conditions. The reasoning engine can also perform natural language processing (NLP) in which the engine leverages NLP techniques to understand and interpret textual data within the network, such as user input, contractual agreements, and communication among participants. This enables the system to process and analyze unstructured data, enhancing its decision-making capabilities. The reasoning engine can also perform adaptive learning in which the reasoning engine continually learns from its interactions and experiences within the network, improving its algorithms and decision-making capabilities over time. This adaptive learning feature allows the server to stay up-to-date with the evolving needs and requirements of the network and its participants. The reasoning engine can also perform various other tasks as described with respect to FIG. 6.

The reasoning engine can also perform anomaly detection in which the reasoning server is capable of detecting anomalies and potential fraudulent activities within the network. The reasoning engine uses machine learning algorithms to identify unusual patterns, irregularities, or deviations from the norm, alerting relevant parties to take necessary action. At step 708, it is determined whether an anomaly is detected. If not, the method 700 moves to step 712. If so, at step 710, the reasoning engine initiates the issuance of an anomaly alert to the one or more parties, such as the patient/consumer 618. In some embodiments, the anomaly alert can be sent by the observer/auditor 614.

At step 712, an ephemeral record management operation(s) is executed during a transaction event. The ephemeral record management operation(s) can be executed by the ephemeral record management system 606. The ephemeral record management operation(s) enforces temporary storage in which, upon receiving sensitive information, the recipient's local storage maintains the data only temporarily. The duration of storage can be predefined by the sender or the network, based on the nature of the information, consumer consent, and legal requirements. In various embodiments, the ephemeral management operation(s) also enforces auto-deletion in which the system automatically deletes the sensitive data from the recipient's local storage after a specified duration or upon the occurrence of a confirmation event. This event can be an acknowledgment from the recipient, completion of a specific task or transaction, or any other predefined trigger agreed upon by the involved parties.

In various embodiments, the ephemeral management operation(s) also enforces data encryption. To further enhance data security, the ephemeral record management operation(s) can incorporate advanced encryption techniques to protect sensitive information during transmission and storage. This ensures that even if unauthorized access occurs, the data remains unintelligible to malicious actors. In various embodiments, the ephemeral management operation(s) also uses audit trails in which the system maintains a comprehensive audit trail of all activities associated with the ephemeral records, including the creation, access, deletion, and unique reference generation. This audit trail enables traceability and accountability, ensuring compliance with regulations and consumer consent requirements. In various embodiments, the ephemeral management operation(s) also enforces access control in which the ephemeral record management operation(s) implements robust access control mechanisms to ensure that only authorized parties can access the sensitive information. This can include authentication, authorization, and role-based access control, as well as the integration of blockchain-based identity management systems.

In various embodiments, the ephemeral management operation(s) also enforces data recovery and backup. In case of system failures or data corruption, the ephemeral record management operation(s) can incorporate data recovery and backup mechanisms, allowing the restoration of critical information without compromising data privacy and security. By integrating these elements and functionalities, the ephemeral record management operation(s) provides a secure, efficient, and privacy-preserving solution for managing sensitive information in the network. The system allows trusted parties to exchange data with consumer consent while minimizing the risk of unauthorized access or data breaches, promoting transparency and trust among network participants.

As noted above, the ephemeral record management operation(s) can enforce that data used locally on client devices for a transaction or other process is only stored temporarily, such that ephemeral data records stored locally on client devices are eventually deleted. At step 714, upon deletion of ephemeral record, a unique reference is generated pointing to original timestamped source. This can include the at least one processing device executing a unique reference generation via the unique reference generation system 610, via the ephemeral record management system 606, or both. In some embodiments, the unique reference generation system 610 can be included in or be a part of the ephemeral record management system 606. The unique reference can be a pointer to the original timestamped source of the data. This pointer enables participants to access the information for legal and reference purposes without storing the sensitive data locally.

The unique reference generation ensures traceability, accountability, and compliance with consumer consent and legal requirements, while maintaining data privacy and security. In various embodiments, the unique reference identifier that points to the original timestamped source of the data can be a hash value, a combination of alphanumeric characters, or any other unique representation that ensures the data's traceability. The unique reference generation can also include performing timestamping in which the unique reference generation includes a timestamp for each reference, indicating the exact time and date when the reference was created. This provides a chronological context for the data access and deletion events for legal and reference purposes. The unique reference generation also can include performing metadata storage in which the system stores metadata associated with the unique reference, such as the sender, recipient, data type, and purpose of the data exchange. This metadata helps provide context for the reference and facilitates traceability and accountability.

At step 716, an observer/auditor in consensus with two or more authorities is added to the unique reference to monitor and audit transactions. The observer/auditor can be the observer/auditor 614. The observer/auditor monitors the exchange of sensitive information within the network, ensuring that data sharing is in compliance with consumer consent and legal requirements. The observer/auditor also performs compliance verification in which the observer/auditor verifies that the network's activities are in accordance with applicable regulations, including data privacy, security, and consumer protection laws. The observer/auditor also performs audit reporting in which the observer/auditor generates and delivers audit reports to relevant parties, such as network participants, authorities, and regulators, providing insights into the network's activities and compliance status. The observer/auditor also performs dispute resolution in which the observer/auditor may play a role, offering an unbiased perspective and assisting in the resolution of disagreements between network participants. The observer/auditor also performs network improvement in which the observer/auditor provides feedback to the network authority and other parties, helping identify areas for improvement and promoting the continuous enhancement of the system.

At step 718, all references to original recipient are tracked via source tracking. This can include the at least one processing device executing the source tracking operation 612. The source tracking results can be used by the observer/auditor during performance of activity monitoring, audit reporting, dispute resolution, etc. At step 720, activity monitoring, audit reporting, dispute resolution, and/or network improvement are performed such as by using the source tracking information, as well as any alerts or other events triggered by the reasoning engine.

Although FIG. 7 illustrates one example of a method 700 for a dynamic network for trusted information exchange, various changes may be made to FIG. 7. For example, while shown as a series of steps, various steps in FIG. 7 could overlap, occur in parallel, occur in a different order, or occur any number of times (including zero times).

Figure 8:
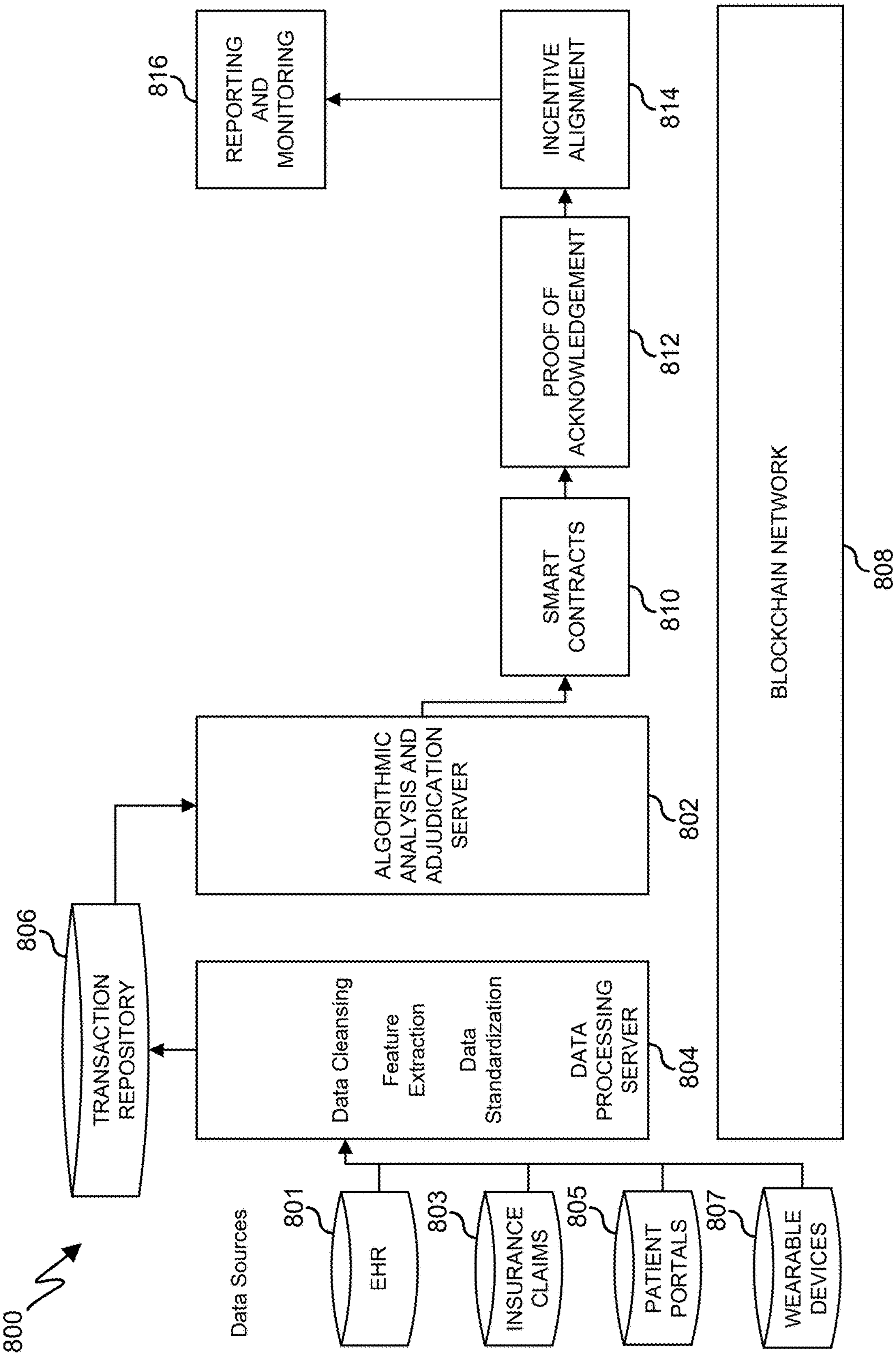
FIG. 8 illustrates an example proof of acknowledgement architecture in accordance with this disclosure.

FIG. 8 illustrates an example proof of acknowledgement architecture 800 in accordance with this disclosure. For ease of explanation, the architecture 800 shown in FIG. 8 is described as being implemented on or supported by the electronic device 101 in the network configuration 100 of FIG. 1. However, the architecture 800 shown in FIG. 8 could be used with any other suitable device(s) and in any other suitable system(s), such as when the architecture 800 is implemented on or supported by the server 106.

The architecture 800 enables performance of distributed consensus and monitoring methods for evaluating needs and providing proof of acknowledgements. For example, the distributed consensus and monitoring methods can evaluate healthcare needs by combining patient health, financial, and engagement data addressing frictions in healthcare value-based care by using a distributed consensus and monitoring method that uses the combined patient health, financial, and engagement data. The architecture 800 also utilizes advanced AI techniques, blockchain technology, and a proof of acknowledgement (PoA) mechanism, to reduce friction, enhance efficiency, and promote transparency.

As shown in FIG. 8, various data sources can be accessed by a data processing server(s) 804 that manipulates the data for use by other components of the architecture 800, such as an adjudication server 802. The various data sources can include as electronic health record (EHR) sources 801, insurance claims sources 803, patient portal sources 805, wearable device sources 807, and/or other data sources. The data processing server can perform data cleansing, feature extraction, data standardization, and/or other operations using the data retrieved from the various data sources.

The adjudication server 802 is integrated into the system to automatically process transactions and resolve disputes or discrepancies. The adjudication server 802 leverages advanced AI algorithms to analyze transaction data, validate the legitimacy of claims, and calculate appropriate reimbursements based on predefined rules and conditions. By automating the adjudication process, the server helps to reduce the time and cost associated with manual claim reviews, enhancing overall efficiency and reducing financial friction. In some embodiments, the architecture 800 can include or be a part of the architectures 200, 400, and/or 600. For example, in some embodiments, the adjudication server 802 can include or be a part of the AI-driven event detection and notification system 211, the reasoning engine 402, and/or the reasoning engine 602.

The architecture 800 can also include a transaction repository 806. The transaction repository 806 is a secure, tamper-proof, repository for storing transactions data and relevant metadata. The transaction repository 806 utilizes blockchain technology supported by a blockchain network 808, and ensures the integrity and traceability of all transactions, enabling parties to review and audit activities with confidence. By leveraging use of the blockchain network 808, the system ensures secure, transparent, and tamper-proof storage of healthcare data. The decentralized nature of the blockchain network 808 promotes trust among parties and streamlines the exchange of information across various entities. The transaction repository 806 also facilitates real-time monitoring and analysis of transaction data, allowing parties to identify patterns, trends, and areas for improvement.

The adjudication server 802 can perform various algorithmic analysis and adjudication operations on the data stored in the transaction repository 806, which can include feature extraction data provided by the data processing server 804 that is formatted for use by one or more machine learning models executed by the adjudication server 802. The adjudication server employs advanced AI algorithms, such as machine learning and natural language processing, to analyze and interpret patient health, financial, and engagement data. This data-driven approach enables the identification of patterns and trends, allowing for more accurate predictions of healthcare needs and resource allocation. Advanced AI algorithms and machine learning techniques are employed to analyze the integrated data, uncovering patterns and trends related to healthcare costs, patient outcomes, and engagement levels.

This analysis helps identify areas of improvement and opportunities for optimizing resource allocation in value-based care. In various embodiments, the adjudication server 802 can also employ advanced AI techniques to identify potential fraudulent activities, such as duplicate billing, overcharging, or misrepresentation of services. By detecting and addressing fraudulent transactions early, the system helps to minimize financial losses and maintain the integrity of the healthcare financial ecosystem. By leveraging AI and machine learning, the architecture 800 enables data-driven decision-making related to financial resource allocation and utilization. This helps to identify inefficiencies, optimize processes, and prioritize value-based care initiatives, ultimately reducing financial friction and enhancing overall healthcare outcomes.

The architecture 800 uses the blockchain network 808 to securely store and share data among parties, ensuring data integrity and promoting trust and transparency. The blockchain network 808 uses a distributed consensus mechanism to assist in establishing agreement on the validity and prioritization of needs and resource allocations. The blockchain network 808 allows for data to be securely stored and shared among parties. For example, nodes of the blockchain network 808 can represent healthcare providers, payers, and other involved parties.

The architecture 800 integrates smart contracts 810 to automate the execution of agreements and transactions based on predefined rules and conditions. This automation reduces the need for manual intervention, decreases transaction costs, and accelerates the overall processes of the architecture 800. In some embodiments, the smart contracts 810 can be used to automate billing and reimbursement processes based on predefined rules and conditions. This automation reduces manual intervention, decreases transaction costs, and accelerates the overall process, further reducing financial friction in the healthcare value-based care ecosystem.

The architecture 800 performs a proof of acknowledgement operation(s) 812 that acts as a consensus protocol to validate the accuracy and integrity of the healthcare data, thereby facilitating a trustworthy exchange of information. The proof of acknowledgement operation 812 minimizes the risk of data manipulation and ensures that all parties involved acknowledge the transactions. The proof of acknowledgement operation 812 validates the completion of specific actions or milestones in certain processes, such as healthcare processes, such as receiving a prescribed treatment, attending a follow-up appointment, or achieving a target health outcome. This validation serves as a basis for transactions and resource allocation decisions, ensuring that funds are directed towards value-based care initiatives that demonstrate tangible results.

The architecture 800 can also perform an incentive alignment operation(s) 814. For example, the incentive alignment operation 814 can link financial rewards and penalties to objective performance metrics and patient outcomes, which can, for example, help to align the incentives of healthcare providers, payers, and patients. This alignment encourages the adoption of evidence-based practices, promotes patient engagement, and fosters a culture of continuous improvement. The architecture 800 can incorporate dynamic incentive models that reward healthcare providers, patients, and other parties for their participation and adherence to value-based care principles. These incentives can be tailored to individual circumstances, ensuring that all parties are motivated to contribute to the improvement of healthcare outcomes.

The architecture 800 can also provide reporting and monitoring service(s) 816. The service 816 offers real-time monitoring and feedback capabilities, enabling healthcare providers to track and evaluate the effectiveness of their interventions, adjust their strategies accordingly, and enhance the overall quality of care. The architecture 800 is designed to integrate seamlessly with existing systems, such as existing healthcare information systems, ensuring smooth data exchange and reducing the friction associated with information silos. Among other benefits, the architecture 800 addresses various aspects of financial friction in healthcare value-based care, which refers to the inefficiencies, delays, and unnecessary costs associated with the allocation and distribution of financial resources in the healthcare sector. By streamlining financial transactions, promoting transparency, and enhancing collaboration among stakeholders, the system can reduce financial friction and optimize resource allocation.

The architecture 800 can integrate seamlessly with current healthcare financial transaction systems, such as electronic health records (EHRs), practice management systems, and billing platforms. This interoperability ensures smooth data exchange and minimizes the friction associated with information silos, allowing healthcare providers, payers, and other parties to collaborate more effectively. The architecture 800 also can support the development and implementation of customizable financial models that cater to the unique needs of various healthcare parties. These models can incorporate factors such as regional variations, population demographics, and specific healthcare objectives, ensuring that financial resources are allocated effectively and efficiently.

Although FIG. 8 illustrates one example of a proof of acknowledgement architecture 800, various changes may be made to FIG. 8. For example, various components and functions in FIG. 8 may be combined, further subdivided, replicated, or rearranged according to particular needs. Also, one or more additional components and functions may be included if needed or desired. For instance, the components 802, 804, 806, 808, 810, 812, 814, and 816 could all be a part of a same server system, such as being a part of one server or multiple servers in a distributed server architecture.

Figure 9:
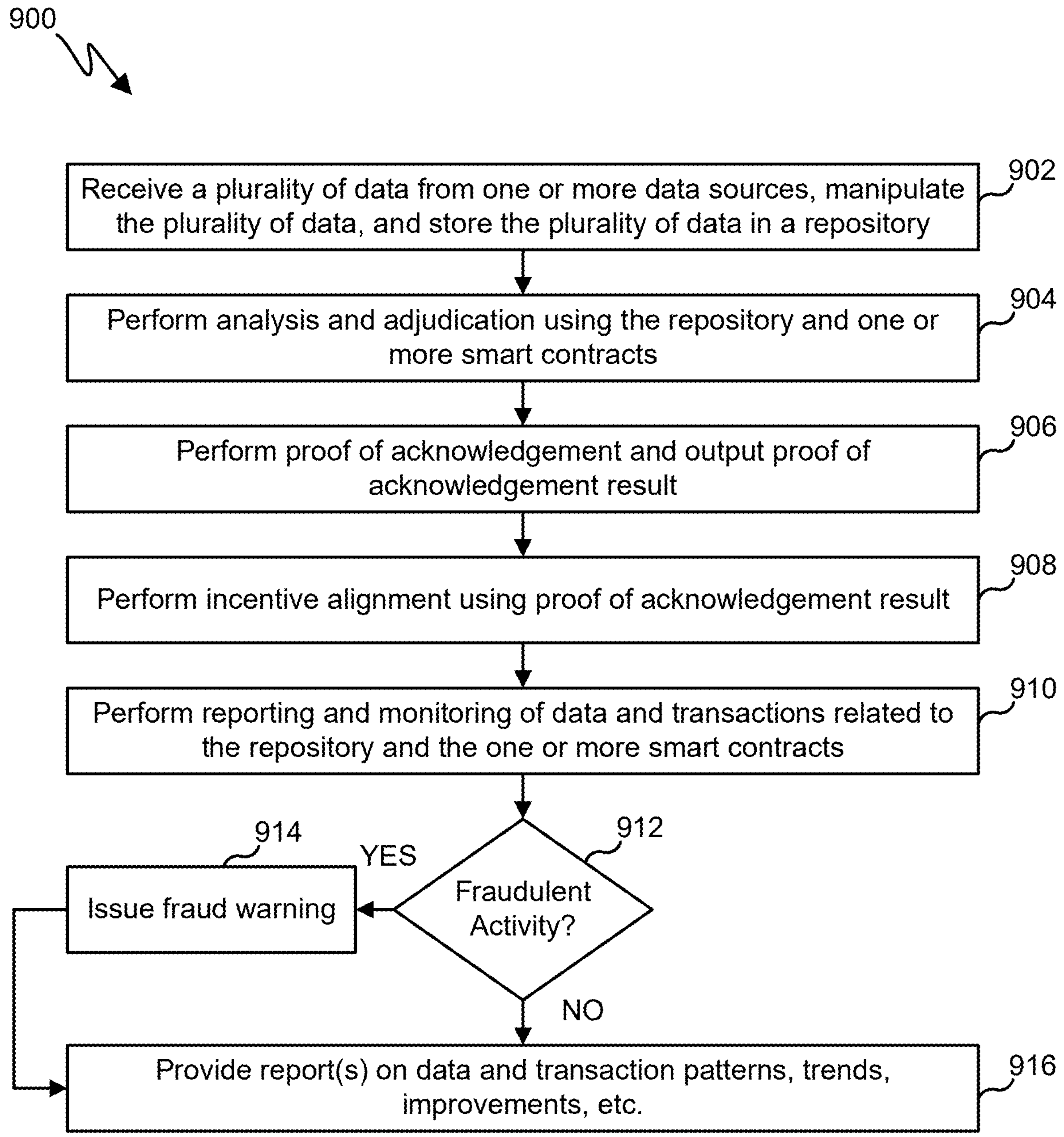
FIG. 9 illustrates an example proof of acknowledgement method in accordance with this disclosure.

FIG. 9 illustrates an example proof of acknowledgement method 900 in accordance with this disclosure. For ease of explanation, the method 900 shown in FIG. 9 is described as being performed using the electronic device 101 in the network configuration 100 of FIG. 1. However, the method 900 could be performed using any other suitable device(s), such as the server 106, and in any other suitable system(s).

At step 902, a plurality of data is received from one or more data sources, the plurality of data is manipulated, and the plurality of data is stored in a repository. This can include the at least one processing device 120 retrieving the plurality of data from the plurality of data sources, such as data sources 801, 803, 805, 807, via a data processing server such as the data processing server 804. This can also include the processing device 120, such as via the data processing server, performing data cleansing, feature extraction, data standardization, and/or other operations using the data retrieved from the various data sources. This can also include the processing device 120 storing the manipulated data in the repository, such as the transaction repository 806.

At step 904, analysis and adjudication is performed using the repository and one or more smart contracts. This can include the at least one processing device 120 algorithmic analysis and adjudication operations on the data stored in the repository, such as via the adjudication server 802. This can also include the at least one processing device 120 consulting the one or more smart contracts, such as smart contracts 810, to automate the execution of agreements and transactions based on predefined rules and conditions and track patterns, trends, etc., and provide reporting on same or on other detected events such as based on fraudulent activity detection.

At step 906, proof of acknowledgement is performed and a proof of acknowledgement result is output. This can include the at least one processing device 120 executing the proof of acknowledgement operation(s) 812 to provide a consensus protocol to validate the accuracy and integrity of the healthcare data, thereby facilitating a trustworthy exchange of information. The proof of acknowledgement operation minimizes the risk of data manipulation and ensures that all parties involved acknowledge the transactions. The proof of acknowledgement operation validates the completion of specific actions or milestones in certain processes, such as healthcare processes, such as receiving a prescribed treatment, attending a follow-up appointment, or achieving a target health outcome. This validation serves as a basis for transactions and resource allocation decisions, ensuring that funds are directed towards value-based care initiatives that demonstrate tangible results.

At step 908, incentive alignment is performed using the proof of acknowledgement result. This can include the at least one processing device 120 executing the incentive alignment operation(s) 814 to link financial rewards and penalties to objective performance metrics and patient outcomes, which can, for example, help to align the incentives of healthcare providers, payers, and patients. This alignment encourages the adoption of evidence-based practices, promotes patient engagement, and fosters a culture of continuous improvement. This can also incorporate dynamic incentive models that reward healthcare providers, patients, and other parties for their participation and adherence to value-based care principles. These incentives can be tailored to individual circumstances, ensuring that all parties are motivated to contribute to the improvement of healthcare outcomes.

At step 910, reporting and monitoring of data and transactions related to the repository and the one or more smart contracts is performed. This can include the at least one processing device 120 executing the reporting and monitoring service(s) 816 to provide real-time monitoring and feedback capabilities, enabling the tracking and evaluation of the effectiveness of healthcare interventions, allowing for adjustment of strategies accordingly, and enhancing the overall quality of care.

At step 912, it is determined whether fraudulent activity is detected. This can include that at least one processing device 120, as part of executing the reporting and monitoring services, and in some embodiments also as part of performing the analysis and adjudication using the adjudication server, employing advanced AI techniques to identify potential fraudulent activities, such as duplicate billing, overcharging, or misrepresentation of services. By detecting and addressing fraudulent transactions early, the system helps to minimize financial losses and maintain the integrity of the healthcare financial ecosystem. Additionally, by leveraging AI and machine learning, the architecture enables data-driven decision-making related to financial resource allocation and utilization. This helps to identify inefficiencies, optimize processes, and prioritize value-based care initiatives, ultimately reducing financial friction and enhancing overall healthcare outcomes.

If, at step 912, no fraudulent activity is detected, the method 900 moves to step 916. If, at step 912, fraudulent activity is detected, at step 914, a fraud warning is issued. The fraud warning can be issued to various parties associated with the subject data and transactions to put them on notice of such possible fraudulent activities so that remedial action can be undertaken. The method then moves to step 916.

At step 916, one or more reports on data and transaction patterns, trends, improvements, etc., are provided. This can include the at least one processing device 120 executing the reporting and monitoring service(s) 816 to provide reports on patterns, trends, possible improvements, etc. related to the data, transactions, and smart contracts to one or more associated parties.

Although FIG. 9 illustrates one example of a proof of acknowledgement method 900, various changes may be made to FIG. 9. For example, while shown as a series of steps, various steps in FIG. 9 could overlap, occur in parallel, occur in a different order, or occur any number of times (including zero times).

It will be understood that the architectures 200, 400, 600, and 800 shown and described with respect to FIGS. 2, 4, 6, and 8 can be combined as part of one architecture in which the processes and methods facilitated by the architectures 200, 400, 600, and 800 can be performed by the one architecture.

It should be noted that the functions shown in or described with respect to FIGS. 2 through 9 can be implemented in an electronic device 101, 102, 104, server 106, or other device(s) in any suitable manner. For example, in some embodiments, at least some of the functions shown in or described with respect to FIGS. 2 through 9 can be implemented or supported using one or more software applications or other software instructions that are executed by the processor 120 of the electronic device 101, 102, 104, server 106, or other device(s). In other embodiments, at least some of the functions shown in or described with respect to FIGS. 2 through 9 can be implemented or supported using dedicated hardware components. In general, the functions shown in or described with respect to FIGS. 2 through 9 can be performed using any suitable hardware or any suitable combination of hardware and software/firmware instructions. Also, the functions shown in or described with respect to FIGS. 2 through 9 can be performed by a single device or by multiple devices.

Although this disclosure has been described with example embodiments, various changes and modifications may be suggested to one skilled in the art. It is intended that this disclosure encompass such changes and modifications as fall within the scope of the appended claims.

What is claimed is:

1. A system comprising:

at least one processing device configured to:

retrieve a plurality of data from one or more data sources;

generate, using a blockchain, a contextual non-fungible token (NFT) based on at least a portion of the plurality of data;

execute one or more ephemeral computing operations in which the at least one processing device is further configured to:

determine whether access to the contextual NFT is allowed under at least one smart contract;

grant, based on the determination, the access to the contextual NFT and associated records pursuant to the at least one smart contract; and analyze, using a reasoning engine configured to execute one or more machine learning models, and based on the at least one smart contract, a transaction event needing consensus among multiple parties;

as a result of deletion of an ephemeral record created during the ephemeral computing operations, generate a unique reference pointing to an original timestamped source of at least a portion of the plurality of data associated with an original recipient;

perform source tracking to track the unique reference associated with the original recipient;

receive results of one or more hybrid transactions stored in a transaction repository using the plurality of data;

determine, using the reasoning engine, a proof of achievement score based on the results of the one or more hybrid transactions;

perform analysis and adjudication using the transaction repository and the at least one smart contract; and determine and output a proof of acknowledgement result based on the analysis and adjudication.

2. The system of claim 1, wherein the at least one processing device is further configured to:

fragment and encrypt a portion of the plurality of data; and generate an electronic record data block from the fragmented and encrypted portion of the plurality of data.

3. The system of claim 2, wherein, to generate the contextual NFT, the at least one processing device is further configured to:

analyze the electronic record data block using the one or more machine learning models of the reasoning engine;

generate the contextual NFT based on the analysis of the electronic record data block; and store information associated with the contextual NFT on the blockchain and create the at least one smart contract governing use of the contextual NFT by one or more parties.

4. The system of claim 3, wherein the at least one processing device is further configured to:

generate and transmit a notification concerning the access to the contextual NFT to a controlling party; and log data concerning the access to the contextual NFT for auditing.

5. The system of claim 1, wherein the at least one processing device is further configured to:

manipulate the plurality of data by at least one of a transformation, a filter, a modification, and a standardization;

train the reasoning engine using the proof of achievement score; and provide based on the proof of achievement score, one or more recommendations.

6. The system of claim 1, wherein the at least one processing device is further configured to:

determine, based on the proof of achievement score, that a consensus is achieved; and transmit an achievement notification indicating the achievement of the consensus.

7. The system of claim 1, wherein the plurality of data includes consent data, and wherein the at least one processing device is further configured to:

create the at least one smart contract based at least in part on the consent data, wherein the analysis using the reasoning engine of the transaction event needing consensus among the multiple parties is based on the consent data; and detect an anomaly based on the analysis of the transaction event and issue an anomaly alert to a controlling party.

8. The system of claim 1, wherein, to perform the source tracking to track the unique reference associated with the original recipient, the at least one processing device is further configured to:

add an observer in consensus with two or more authorities to the unique reference to monitor and audit transactions; and perform at least one of activity monitoring, audit reporting, dispute resolution, and network improvement operations using the observer.

9. The system of claim 1, wherein the at least one processing device is further configured to provide incentive alignment using the proof of acknowledgement result, including creating a link between a determined performance metric and one or more rewards and penalties.

10. The system of claim 1, wherein the at least one processing device is further configured to:

monitor data and transactions related to the transaction repository and the at least one smart contract;

determine fraudulent activity is detected and issue a fraud warning to a controlling party in response; and provide one or more reports on the data and transactions, wherein the one or more reports include at least one of patterns, trends, and improvements data.

11. A method comprising:

retrieving a plurality of data from one or more data sources;

generating, using a blockchain, a contextual non-fungible token (NFT) based on at least a portion of the plurality of data;

executing one or more ephemeral computing operations, including:

determining whether access to the contextual NFT is allowed under at least one smart contract;

granting, based on the determination, the access to the contextual NFT and associated records pursuant to the at least one smart contract; and analyzing, using a reasoning engine configured to execute one or more machine learning models, and based on the at least one smart contract, a transaction event needing consensus among multiple parties;

as a result of deletion of an ephemeral record created during the ephemeral computing operations, generating a unique reference pointing to an original timestamped source of at least a portion of the plurality of data associated with an original recipient;

performing source tracking to track the unique reference associated with the original recipient;

receiving results of one or more hybrid transactions stored in a transaction repository using the plurality of data;

determining, using the reasoning engine, a proof of achievement score based on the results of the one or more hybrid transactions;

performing analysis and adjudication using the transaction repository and the at least one smart contract; and determining and outputting a proof of acknowledgement result based on the analysis and adjudication.

12. The method of claim 11, further comprising:

fragmenting and encrypting a portion of the plurality of data; and generating an electronic record data block from the fragmented and encrypted portion of the plurality of data.

13. The method of claim 12, wherein generating the contextual NFT includes:

analyzing the electronic record data block using the one or more machine learning models of the reasoning engine;

generating the contextual NFT based on the analysis of the electronic record data block; and storing information associated with the contextual NFT on the blockchain and creating the at least one smart contract governing use of the contextual NFT by one or more parties.

14. The method of claim 13, further comprising:

generating and transmitting a notification concerning the access to the contextual NFT to a controlling party; and logging data concerning the access to the contextual NFT for auditing.

15. The method of claim 11, further comprising:

manipulating the plurality of data by at least one of a transformation, a filter, a modification, and a standardization;

training the reasoning engine using the proof of achievement score; and providing based on the proof of achievement score, one or more recommendations.

16. The method of claim 11, further comprising:

determining, based on the proof of achievement score, that a consensus is achieved; and transmitting an achievement notification indicating the achievement of the consensus.

17. The method of claim 11, wherein the plurality of data includes consent data, and the method further comprising:

creating the at least one smart contract based at least in part on the consent data, wherein the analysis using the reasoning engine of the transaction event needing consensus among the multiple parties is based on the consent data; and detecting an anomaly based on the analysis of the transaction event and issue an anomaly alert to a controlling party.

18. The method of claim 11, wherein performing the source tracking to track the unique reference associated with the original recipient includes:

adding an observer in consensus with two or more authorities to the unique reference to monitor and audit transactions; and performing at least one of activity monitoring, audit reporting, dispute resolution, and network improvement operations using the observer.

19. The method of claim 11, further comprising providing incentive alignment using the proof of acknowledgement result, including creating a link between a determined performance metric and one or more rewards and penalties.

20. The method of claim 11, further comprising:

monitoring data and transactions related to the transaction repository and the at least one smart contract;

determining fraudulent activity is detected and issue a fraud warning to a controlling party in response; and providing one or more reports on the data and transactions, wherein the one or more reports include at least one of patterns, trends, and improvements data.

* * * * *